US008268017B2

(12) United States Patent
Ueda et al.

(10) Patent No.: US 8,268,017 B2
(45) Date of Patent: Sep. 18, 2012

(54) METHOD FOR STABILIZING LEUCO-TYPE COLORANT

(75) Inventors: Shigeru Ueda, Tokyo (JP); Takeshi Matsuoka, Tokyo (JP); Akihiko Kan, Ibaraki (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/034,793

(22) Filed: Feb. 21, 2008

(65) Prior Publication Data

US 2008/0295259 A1    Dec. 4, 2008

(30) Foreign Application Priority Data

Feb. 22, 2007   (JP) ................................. 2007-041551

(51) Int. Cl.
*C09B 67/00*    (2006.01)
*D06P 5/00*    (2006.01)
*G01N 33/72*    (2006.01)
*G03C 8/00*    (2006.01)
*C08B 37/16*    (2006.01)
*C12N 9/00*    (2006.01)
*C12Q 1/00*    (2006.01)
*C12Q 1/37*    (2006.01)
*C12Q 1/26*    (2006.01)

(52) U.S. Cl. .................. 8/568; 8/400; 436/66; 430/224; 536/103; 435/4; 435/23; 435/25; 435/183

(58) Field of Classification Search .............. 8/401, 587, 8/636, 400, 568; 436/66; 430/224; 536/103; 435/4, 23, 25, 183
See application file for complete search history.

(56) References Cited

U.S. PATENT DOCUMENTS

| 4,361,108 | A | * | 11/1982 | Robillard et al. ............. 118/265 |
| 4,647,532 | A | | 3/1987 | Watanabe et al. |
| 4,837,331 | A | | 6/1989 | Yamanishi et al. |
| 5,089,420 | A | * | 2/1992 | Albarella et al. ............... 436/66 |
| 5,334,382 | A | | 8/1994 | Phillips et al. |
| 5,370,990 | A | | 12/1994 | Satniford et al. |
| 5,792,736 | A | | 8/1998 | Nakayama et al. |
| 5,902,731 | A | | 5/1999 | Ouyang et al. |
| 6,255,061 | B1 | | 7/2001 | Mori et al. |
| 6,352,835 | B1 | | 3/2002 | Komori et al. |
| 6,586,199 | B2 | | 7/2003 | Ouyang et al. |
| 6,790,665 | B2 | | 9/2004 | Yonehara et al. |
| 7,018,823 | B2 | | 3/2006 | Kurosawa et al. |
| 7,025,734 | B1 | | 4/2006 | Ellis et al. |
| 7,070,948 | B1 | | 7/2006 | Sakaue et al. |
| 7,235,378 | B2 | | 6/2007 | Yonehara |
| 7,250,269 | B2 | | 7/2007 | Kouzuma et al. |
| 7,588,910 | B2 | | 9/2009 | Matsuoka et al. |
| 2003/0175232 | A1 | | 9/2003 | Elliott et al. |
| 2003/0186346 | A1 | | 10/2003 | Yagi et al. |
| 2004/0063213 | A1 | | 4/2004 | Hirai et al. |
| 2004/0205900 | A1 | | 10/2004 | Yagi et al. |
| 2005/0053870 | A1 | * | 3/2005 | Willard et al. ................ 430/332 |
| 2005/0101771 | A1 | | 5/2005 | Kouzuma et al. |
| 2005/0130251 | A1 | * | 6/2005 | Okabe et al. ..................... 435/28 |
| 2005/0221415 | A1 | | 10/2005 | Yonehara et al. |
| 2005/0244926 | A1 | | 11/2005 | Kurosawa et al. |
| 2005/0260735 | A1 | | 11/2005 | Yonehara et al. |
| 2007/0026523 | A1 | * | 2/2007 | Taniguchi et al. .............. 436/18 |
| 2007/0037243 | A1 | | 2/2007 | Hirokawa et al. |
| 2007/0134754 | A1 | | 6/2007 | Hirai |
| 2007/0224685 | A1 | * | 9/2007 | Kouzuma et al. .............. 436/66 |
| 2008/0113381 | A1 | | 5/2008 | Matsuoka et al. |
| 2008/0241816 | A1 | * | 10/2008 | Taniguchi et al. ................ 435/4 |
| 2008/0295259 | A1 | | 12/2008 | Ueda et al. |

FOREIGN PATENT DOCUMENTS

| CN | 1501981 | 6/2004 |
| EP | 0 439 208 A2 | 7/1991 |
| EP | 0 506 386 | 9/1992 |
| EP | 0 526 150 | 2/1993 |
| EP | 0729031 | 8/1996 |
| EP | 1 223 224 | 7/2002 |
| EP | 1 308 787 | 5/2003 |
| EP | 1607475 | 12/2005 |
| EP | 1 626 088 | 2/2006 |
| EP | 1 679 378 | 7/2006 |
| EP | 1 693 461 | 8/2006 |
| EP | 1 693 463 | 8/2006 |

(Continued)

OTHER PUBLICATIONS

Japanese Office Action (Notice for Reasons of Rejection) issued with respect to Japanese Patent App. No. 2005-506428; issued Mar. 10, 2010, along with a partial English language translation. Kouzuma et al., "An Enzymatic Method for the Measurement of Glycated Albumin in Biological Samples", Clinica Chimica Acta, vol. 324, pp. 61-71, 2002.

Wiss, "Untersuchung über Proteasen. 1. Aminosäuren, Blausäure and Pyrophosphat als Effektoren des Pepsin," Helvetica Chimica Acta, vol. 29, pp. 237-246, 1946.

Veierskov et al., "Metabolism of Oat Leaves During Senescence," Plant Physiology, vol. 78, No. 2, pp. 315-319, 1985.

(Continued)

*Primary Examiner* — Harold Pyon
*Assistant Examiner* — Tanisha Diggs
(74) *Attorney, Agent, or Firm* — Greenblum & Bernstein, P.L.C.

(57) ABSTRACT

Provided are a method of stabilizing a leuco dye storable as a liquid for a long time, a method of reducing nonspecific color development thereof at a time of a color development reaction, and a stable liquid reagent composition using the methods. The inventors of the present invention found that coexistence of the leuco dye with a specific reducing agent resulted in suppression of self color development and its remarkably improved stability in a solution, and that when a color development reaction of the leuco dye with hydrogen peroxide was performed, coexistence of the leuco dye, in a reaction solution, with another dye which had an absorption spectrum not influencing a measurement wavelength of the leuco dye and did not react with hydrogen peroxide suppressed nonspecific color development and lowered a reagent blank value, which was applied to an analytical reagent.

12 Claims, 4 Drawing Sheets

FOREIGN PATENT DOCUMENTS

| | | |
|---|---|---|
| EP | 1693462 | 8/2006 |
| EP | 1726660 | 11/2006 |
| EP | 1 767 942 A1 | 3/2007 |
| EP | 1 788 081 | 5/2007 |
| EP | 2 108 952 A1 | 10/2009 |
| GB | 2 348 433 | 10/2000 |
| JP | 58-187858 | 11/1983 |
| JP | 60-200167 | 10/1985 |
| JP | 63-243879 A | 10/1988 |
| JP | 1-118768 | 5/1989 |
| JP | 4-213064 | 8/1992 |
| JP | 4-262796 | 9/1992 |
| JP | 6-086698 A | 3/1994 |
| JP | 6-165696 | 6/1994 |
| JP | 8-089291 | 4/1996 |
| JP | 8-262027 | 10/1996 |
| JP | 11-209795 | 8/1999 |
| JP | 2000-093199 | 4/2000 |
| JP | 3034698 | 4/2000 |
| JP | 2000-175699 A | 6/2000 |
| JP | 2000-210100 | 8/2000 |
| JP | 2001-095598 | 4/2001 |
| JP | 2001-204495 | 7/2001 |
| JP | 2001-292795 | 10/2001 |
| JP | 2002-315600 | 10/2002 |
| JP | 2003-232789 | 8/2003 |
| JP | 2003-235585 | 8/2003 |
| JP | 2004-143240 | 5/2004 |
| JP | 2004-275013 | 10/2004 |
| JP | 2005-110507 | 4/2005 |
| JP | 2005-110657 | 4/2005 |
| JP | 2005-179547 | 7/2005 |
| JP | 2005-264100 | 9/2005 |
| JP | 2005-298545 | 10/2005 |
| JP | 2005-331372 A | 12/2005 |
| JP | 2006-340684 A | 12/2006 |
| JP | 2007-029094 A | 2/2007 |
| WO | 01/18165 | 3/2001 |
| WO | 01/25475 | 4/2001 |
| WO | 02/06519 | 1/2002 |
| WO | 02/21142 | 3/2002 |
| WO | 02/27012 | 4/2002 |
| WO | 02/27330 | 4/2002 |
| WO | 02/27331 | 4/2002 |
| WO | 02/061119 | 8/2002 |
| WO | 03/033601 | 4/2003 |
| WO | 03/107011 | 12/2003 |
| WO | 2004/007760 | 1/2004 |
| WO | 2004/083360 | 9/2004 |
| WO | 2004/104203 | 12/2004 |
| WO | 2005/028660 | 3/2005 |
| WO | 2005/049857 | 6/2005 |
| WO | 2005/049858 | 6/2005 |
| WO | 2005/056823 | 6/2005 |
| WO | 2005/087946 | 9/2005 |
| WO | WO2005088305 | * 9/2005 |
| WO | 2005/121795 A1 | 12/2005 |
| WO | 2006/013921 | 2/2006 |
| WO | 2006/013921 A1 | 2/2006 |
| WO | 2007/083703 | 7/2007 |
| WO | 2008-093722 A1 | 8/2008 |

OTHER PUBLICATIONS

Pillai et al., "Enzymatic Digestion—A Safe and Rapid Technique for Individual Separation of *Macrobrachium rosenbergii* Embryos for Cryopreservation Studies," Cryobiology, vol. 47, No. 3, pp. 242-246, 2003.

Japanese Office Action dated Jun. 30, 2010 that issued with respect to Japanese Patent Application No. 2007-041551, along with a partial English language translation thereof.

English Language Abstract of JP 1-118768 from the Thompson Corporation on STN, May 11, 1989.

English language Abstract of JP 1-118768 from the Japanese Patent Office, May 11, 1989.

English language Abstract of JP 2005-110507, Apr. 28, 2005.

English language Abstract of JP 2004-257013, Oct. 7, 2004.

English language Abstract of JP 2001-095598, Apr. 10, 2001.

English language Abstract of JP 2003-235585, Aug. 26, 2003.

English language Abstract of JP 2005-110657, Apr. 28, 2005.

Sakurabayashi et al., *Clinical Chemistry*, 49(2):269-274 (2003).

Jeppsson et al., *Clinical Chemistry and Laboratory Medicine*, 40(1):78-89 (2002).

Uemoto, *Rinsyokensa (Journal of Medical Technology,)* 46(7):729-734 (2002), and an English language Abstract of the same.

Japanese Official Action issued with respect to Japanese Patent Application 2006-531538 dated Mar. 17, 2011.

Office action that issued with respect to Chinese Patent Application No. 201010255071.8, dated May 12, 2011 along with an english translation thereof.

\* cited by examiner y = 0.9997x − 0.138
$R^2$ = 0.955 y = 0.9927x + 0.0246
$R^2$ = 0.9884

METHOD FOR STABILIZING LEUCO-TYPE COLORANT

CROSS-REFERENCE OF RELATED APPLICATION

This application is an application claiming priority based on Japanese Patent Application No. 2007-041551 filed on Feb. 22, 2007 in Japan, the content of which is incorporated hereinto by reference.

BACKGROUND OF THE INVENTION

1. Field of the Invention

The present invention relates to a method of stabilizing a leuco dye in a solution, a method of reducing nonspecific color development at the time of a color development reaction, and an analytical reagent composition using the methods.

2. Description of the Related Art

In the clinical examination field, various measurement methods using an enzymatic method are established. Among the measurement methods, when using an oxidase, there has been conventionally known a method which involves causing a dye to oxidatively generate in the presence of peroxidase using a generated hydrogen peroxide and various oxidation color development agents, and measuring the absorbance. For example, the combination of a coupler typified by 4-aminoantipyrine and various trinder reagents is frequently used. In contrast, as a method of detecting a smaller amount of hydrogen peroxide at high sensitivity, there has also been known a method which uses a leuco compound such as 2,2'-azino-bis (3-ethylbenzothiazoline-6-sulfonic acid (ABTS). In general, such high sensitivity color development dyes, which are generally referred to as a leuco dye, have poor stability in a solution state and develop self coloring. Therefore, the duration of use is short after the preparation of a reagent, and, moreover, a reagent blank is likely to increase, which causes a problem with the measurement accuracy. Thus, such high sensitivity color development dyes have hardly been put into practical use as a clinical examination reagent kit and the like. As a method of stabilizing a leuco dye which has been reported until now, Japanese Patent Application Laid-open No. 01-118768 (Patent Document 1) reports a stabilization effect of 10-(carboxymethylaminocarbonyl)-3,7-bis(dimethylamino)phenothiazine sodium (DA-67) by cyclodextrin and the derivatives thereof. Moreover, International Patent WO 2003/033601 (Patent Document 2) discloses a method which involves causing peroxidase or fructosyl amino acid oxidase to coexist so as to stabilize a leuco dye N-(carboxymethylaminocarbonyl)-4,4'-bis(dimethylamino)biphenylamine sodium (DA-64). Further, Japanese Patent Application Laid-open No. 2005-110507 (Patent Document 3) discloses a method of stabilizing N,N,N',N',N'',N''-hexa(3-sulfopropyl)-4,4',4''-triaminotriphenylmethane-6Na (TPM-PS).

According to Japanese Patent Application Laid-open No. 01-118768 (Patent Document 1), although the stabilization effect when stored for a short period of time (ten days or shorter) is recognized, there is no disclosure about the behavior when stored for a long period of time. Thus, the stabilization effect when stored for a long period of time is problematic. Further, according to International Patent WO 2003/033601 (Patent Document 2), although it is determined that a dye is stable only based on a spectrum of wavelength, there is no disclosure about whether the quantity of hydrogen peroxide has been actually determined successfully using this. Further, according to Japanese Patent Application Laid-open No. 2005-110507 (Patent Document 3), the stabilization effect by a specific buffer solution and a specific chelating agent is shown. However, the absorbance after stored for a short period of time is measured, and then the stabilization effect after one year is estimated simply by performing proportional calculation using the absorbance. Therefore, the basis for determining the stabilization effect is not sufficient, and the stabilizing effect when actually stored for a long period of time is in doubt.

In contrast, even when stabilization is achieved by a single use of a leuco dye, there is a problem that the dye develops color in a nonspecific manner at the time of the color development reaction of hydrogen peroxide to which peroxidase has been added, which impairs exact measurement. More specifically, in a state where a leuco dye and peroxidase coexist at the time of the color development reaction of hydrogen peroxide, there is a problem that a reagent blank increases with time by a nonspecific reaction even when hydrogen peroxide does not exist.

Since the leuco dye is suitable for high sensitivity detection of hydrogen peroxide, a method of stabilizing the leuco dye which is stable in a liquid state for a long period of time is desired.

[Patent Document 1] Japanese Patent Application Laid-open No. 01-118768
[Patent Document 2] WO 2003/033601
[patent Document 3] Japanese Patent Application Laid-open No. 2005-110507

SUMMARY OF THE INVENTION

The present invention aims to provide a method of stabilizing a leuco dye which can be stored in a liquid state for a long period of time, a method of reducing nonspecific color development at the time of a color development reaction of a leuco dye, and an analytical reagent composition which is stable in a liquid state using the methods.

The inventors of the present invention conducted extensive research, and, as a result, found that self coloring was suppressed by causing a leuco dye to coexist with a specific reducing agent, and the stability in a liquid state was markedly improved.

Moreover, the inventors of the present invention found that nonspecific coloring was surprisingly suppressed, a reagent blank value decreased, and the variation in the reagent blank values was sharply reduced to thereby remarkably improve the measurement accuracy when another dye which has an absorption spectrum which does not influence on a measurement wavelength of a leuco dye at the time of a color development reaction with hydrogen peroxide using a leuco dye and which does not react with hydrogen peroxide are made to coexist in a reaction liquid.

Further, the present invention was applied to an analytical reagent, and thus a reagent composition was accomplished which was stable in a liquid state in an enzymatic measurement method of hemoglobin A1 c which was a glycated protein.

Specifically, the present invention has the following constructions:

(1) a method of stabilizing a leuco dye solution, in which a leuco dye coexists with at least one of reducing agents selected from the group consisting of reductive thioalcohols and reductive sulfates;

(2) a method of stabilizing a leuco dye solution according to item (1), in which the leuco dye includes 10-(carboxymethylaminocarbonyl)-3,7-bis(dimethylamino)phenothiazine sodium or N,N,N',N',N",N"-hexa(3-sulfopropyl)-4,4',4"-triaminotriphenylmethane.6 sodium;

(3) a method of stabilizing a leuco dye solution according to item (1) or (2), in which a concentration of the leuco dye in a solution is 0.01 to 2 mM;

(4) a method of stabilizing a leuco dye solution according to any one of items (1) to (3), in which a concentration of the reducing agent in a solution is 0.005 to 10 mM;

(5) a method of stabilizing a leuco dye solution according to any one of items (1) to (4), in which the reducing agent includes at least one of kinds selected from the group consisting of cysteine, cysteamine, N-acetylcysteine, thioglycerol, sodium thiosulfate, sodium sulfite, and sodium disulfite;

(6) a liquid composition of a leuco dye, including: at least one of reducing agents selected from the group consisting of 0.005 to 10 mM reductive thioalcohols and reductive sulfates; and 0.01 to 2 mM of 10-(carboxymethylaminocarbonyl)-3,7-bis (dimethylamino)phenothiazine sodium or N,N,N',N',N", N"-hexa(3-sulfopropyl)-4,4',4"-triaminotriphenylmethane.6 sodium;

(7) a liquid composition according to item (6), in which the reducing agent is at least one of kinds selected from the group consisting of cysteine, cysteamine, N-acetylcysteine, thioglycerol, sodium thiosulfate, sodium sulfite, and sodium disulfite;

(8) a method of reducing a nonspecific color development reaction of a leuco dye, in which the leuco dye coexists with another dye in a color development reaction of hydrogen peroxide in the copresence of peroxidase using the leuco dye, the another dye having an absorption spectrum not influencing on a measurement wavelength of a leuco dye and not reacting with hydrogen peroxide;

(9) a method of reducing a nonspecific color development reaction of a leuco dye according to item (8), in which a maximum absorption wavelength of the another dye which has an absorption spectrum not influencing on a measurement wavelength of a leuco dye and does not react with hydrogen peroxide is in a range of 400 nm to 550 nm;

(10) a method of reducing a nonspecific color development reaction of a leuco dye according to item (8) or (9), in which the another dye which has an absorption spectrum not influencing on a measurement wavelength of a leuco dye and does not react with hydrogen peroxide includes at least one of kinds selected from Orange G. Orange II, Food Red No. 2, Food red No. 3, Food Red No. 40, Food Red No. 102, Food Red No. 104, Food Red No. 106, Food Yellow No. 4, and Food Yellow No. 5;

(11) a method of reducing a nonspecific color development reaction of a leuco dye according to any one of items (8) to (10), in which the leuco dye includes 10-(carboxymethylaminocarbonyl)-3,7-bis(dimethylamino)phenothiazine sodium or N,N,N',N',N",N"-hexa(3-sulfopropyl)-4,4',4"-triamino triphenylmethane.6 sodium;

(12) a method of quantifying hydrogen peroxide, including reacting a leuco dye with hydrogen peroxide in a state where the leuco dye coexists with at least one of reducing agents selected from the group consisting of reductive thioalcohols and reductive sulfates and another dye which has an absorption spectrum not influencing on a measurement wavelength of the leuco dye and does not react with hydrogen peroxide;

(13) a reagent for quantifying hydrogen peroxide, in which the reagent is formed of a combination of a reagent containing another dye which has an absorption spectrum not influencing on a measurement wavelength of a leuco dye and does not react with hydrogen peroxide and peroxidase and another reagent containing a leuco dye and at least one of reducing agents selected from the group consisting of reductive thioalcohols and reductive sulfates;

(14) a liquid and stable reagent for measuring a glycated protein using a reagent for quantifying hydrogen peroxide according to item (13);

(15) a reagent for measuring a glycated protein according to item (14), in which the reagent is formed of a combination of: a reagent containing, as a leuco dye, 10-(carboxymethylaminocarbonyl)-3,7-bis(dimethylamino)phenothiazine sodium or N,N,N',N',N",N"-hexa(3-sulfopropyl)-4,4',4"-triaminotriphenylmethane.6 sodium, at least one of reducing agents selected from the group consisting of reductive thioalcohols and reductive sulfates, and protease which acts on a glycated protein; and another reagent containing peroxidase, another dye which has an absorption spectrum not influencing on a measurement wavelength of a leuco dye and does not react with hydrogen peroxide, and ketoamine oxidase;

(16) a reagent for measuring a glycated protein according to item (14), in which the glycated protein includes hemoglobin A1c; and a total hemoglobin is quantified with the first reagent, and a hemoglobin A1c is quantified with the second reagent, whereby a ratio of an amount of the hemoglobin A1c to the total hemoglobin amount is determined;

(17) a reagent for measuring a glycated protein according to item (16), including: a first reagent containing a protease reaction accelerator, ketoamine oxidase which acts on 1-deoxyfructosyl-L-valyl-L-histidine, peroxidase, a trinder reagent, ascorbate oxidase, and another dye which has an absorption spectrum not influencing on a measurement wavelength of leuco dye and does not react with hydrogen peroxide; and a second reagent containing protease which can cleave 1-deoxyfructosyl-L-valyl-L-histidine from a glycated β chain terminal of the hemoglobin A1c, 10-(carboxymethylaminocarbonyl)-3,7-bis(dimethylamino)phenothiazine sodium, cyclodextrins, and at least one of reducing agents selected from the group consisting of reductive thioalcohols and reductive sulfates;

(18) a reagent for measuring a glycated protein according to item (16), including: a first reagent containing a protease reaction accelerator, protease which acts on the hemoglobin A1c to cleave 1-deoxyfructosyl-L-valyl-L-histidine from a glycated β chain terminal of the hemoglobin A1 c, 10-(carboxymethylaminocarbonyl)-3,7-bis(dimethylamino)phenothiazine sodium, catalase, cyclodextrins, and a reducing agent; and a second reagent containing ketoamine oxidase, peroxidase, and a dye which has an absorption spectrum not influencing on a measurement wavelength of a leuco dye and does not react with hydrogen peroxide;

(19) a reagent for measuring a glycated protein according to item (17), in which the protease reaction accelerator includes an anionic surfactant selected from N-acylamino acid (salt) or N-acyl taurine (salt), the ketoamine oxidase is derived from *Neocosmospora* or *Curvularia*, the dye which has an absorption spectrum not influencing on a measurement wavelength of a leuco dye and does not react with hydrogen peroxide includes Yellow No. 4, Red No. 40, or Red No. 102, the protease which acts on the hemoglobin A1c to cleave 1-deoxyfructosyl-L-valyl-L-histidine from a glycated β chain terminal of the hemoglobin A1c is derived from *Bacillus* or *Rhizobacter*, the cyclodextrins include 2-hydroxypropyl-β-cyclodextrin, the trinder reagent includes ALPS or ADPS, and the reducing agent includes sodium sulfite, and, a hemocyte is hemolyzed with water to be used as a specimen; and

(20) a reagent for measuring a glycated protein according to item (17), in which the reagent measures a glycated protein in whole blood, and the first reagent further contains ketoamine oxidase.

The present invention provides a method of stabilizing a leuco dye in a solution, a method of reducing nonspecific color development at the time of a color development reaction, and an analytical reagent composition for glycated protein using the methods.

DETAILED DESCRIPTION OF THE PREFERRED EMBODIMENTS

Figure 1:
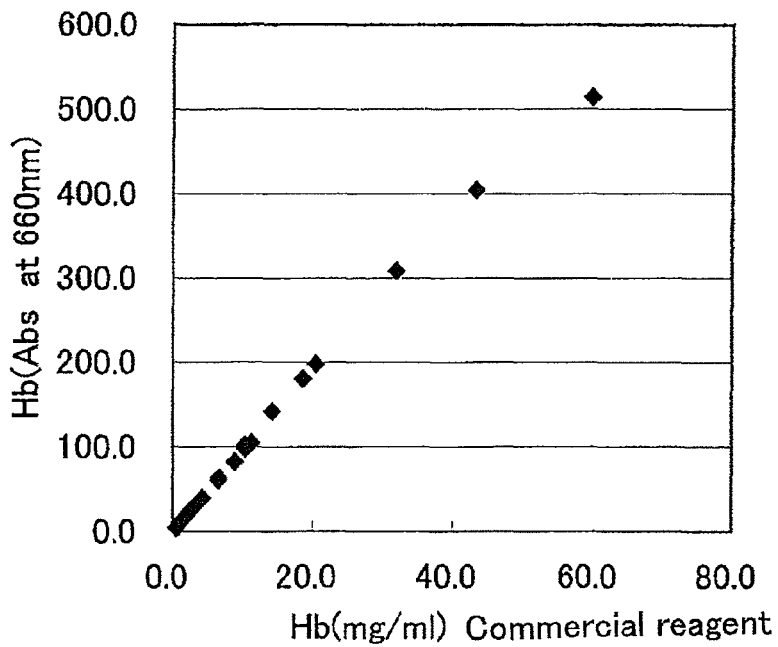
FIG. 1 is a graph illustrating the measured amount of a total hemoglobin by a protease reaction accelerator described in WO 2006/013921 (Patent Document 12).

Hereinafter, the present invention will be specifically described.

In general, it is known that a reducing agent impedes a color development reaction of an oxidation color development dye such as a leuco dye and hydrogen peroxide by peroxidase to thereby cause lowering of color intensity. Therefore, even when a leuco dye is stabilized by the addition of a reducing agent, there may arise a case where the color intensity lowers and thus the addition of a reducing agent is not practical. A degree of color development inhibition by such a reducing agent varies depending on the type of the oxidation color development dye. Therefore, it is desirable that a leuco dye which can be used in the present invention be less susceptible to color development inhibition by a reducing agent added as a stabilizing agent or show a stabilization effect even when the concentration of a reducing agent is low.

As a suitable example of the leuco dye which can be used for the present invention, 10-(carboxymethylaminocarbonyl)-3,7-bis(dimethylamino)phenothiazine sodium (DA-67) or N,N,N',N',N'',N''-hexa(3-sulfopropyl)-4,4',4''-triaminotriphenylmethane.6 sodium (TPM-PS) is mentioned. The concentration of the leuco dye is, for example, in the range of 0.005 to 10 mM, preferably in the range of 0.02 to 3 mM, and more preferably in the range of 0.05 to 1 mM.

Next, as the reducing agent which can be used in the present invention, reductive thioalcohols and reductive sulfates are mentioned. Mentioned as the reductive thioalcohols are thioglycerol, cysteine, N-acetylcysteine, cysteamine hydrochloride (2-aminoethanethiol hydrochloride). Mentioned as the reductive sulfates are sodium thiosulfate, potassium thiosulfate, sodium sulfite, potassium sulfite, sodium disulfite, potassium disulfite, etc. These substances can be used singly or in combination.

The concentration of such reducing agents may be determined with reference to a concentration range of a target measured substance after experimentally confirming a degree of color development inhibition and a stabilization degree by the selected reducing agent. For example, the concentration of such reducing agents is in the range of 0.005 to 10 mM, and preferably in the range of 0.02 to 3 mM.

Further, a synergistic effect can also be expected by combining the reducing agent with conventionally-known stabilizing agents such as cyclodextrin and its derivatives.

Thus, by causing the leuco dye to coexist with the reducing agent, stabilization of the leuco dye which does not color for a long period of time in a solution state was achieved. This made it possible to apply the leuco dye to a practical and higher-precision analytical reagent. As a suitable example in this case, the reagents are classified into two kinds of reagents, and then a solution in which the leuco dye of the present invention and the reducing agent are made to coexist may be used for one kind of reagent, and a peroxidase solution may be used for the other kind of reagent.

In contrast, as previously described, even when the stabilization of the leuco dye was achieved, there was a problem that the leuco dye developed color in a nonspecific manner at the time of the color development reaction of hydrogen peroxide to which peroxidase was added, which impaired exact measurement. More specifically, even when hydrogen peroxide does not exist in a state where the leuco dye and peroxidase coexist at the time of the color development reaction of hydrogen peroxide, a reagent blank increases with time due to a nonspecific reaction. In general, in order to quantitatively measure the color intensity, a spectrophotometric assay method is used, which involves emitting light to a reaction solution to thereby measure the absorbance at a wavelength peculiar to each oxidation dye. For example, 10-(carboxymethylaminocarbonyl)-3,7-bis(dimethylamino)phenothiazine sodium (DA-67) has the maximum absorption wavelength near 660 nm, and N,N,N',N',N'',N''-hexa(3-sulfopropyl)-4,4',4''-triaminotriphenylmethane.6Na (TPM-PS) has the maximum absorption wavelength near 600 nm.

The inventors of the present invention imagined that since light to be emitted as a light source for measuring the absorbance formed a cause of a reagent blank, the reagent blank was greatly influenced by the intensity, optical path length, etc. of a light source lamp of an analyzer. In order to confirm this, the inventors investigated using two kinds of automatic analyzers, whose specifications were different from each other, and found that the reagent blank values were actually different sharply from each other. It became clear that the reagent blank value was greatly influenced by the specification of an analyzer, for example, mainly influenced by the output of a light source lamp and the quantity of light irradiated to a reaction mixture. However, in practical use, there arose a problem that when the reagent blank was higher, the accuracy of measurement decreased. It was presumed that even when the leuco dye was able to be stabilized in a solution by causing a specific reducing agent to coexist, the reagent blank was influenced by a light source lamp in the process of irradiating the light source lamp to monitor the absorbance by the spectrophotometric assay method when an actual color development reaction advanced in the coexistence of peroxidase. As a result, the reagent blank probably increased as a nonspecific color development to thereby reduce the measurement accuracy.

Thus, the inventors of the present invention conducted extensive research and, as a result, found that, by causing a dye which had the maximum absorption wavelength near 400 to 550 nm to coexist in a reaction liquid so as to reduce the influence of the light source lamp at the time of photometry during the color development reaction of hydrogen peroxide using the leuco dye, the nonspecific color development was surprisingly suppressed, the reagent blank value decreased, and the variation in the reagent blank values sharply reduced to thereby markedly improve the measurement accuracy.

The dye of the present invention which has an absorption spectrum which does not influence on a measurement wavelength of the leuco dye and does not react with hydrogen peroxide refers to a dye which does not develop self-oxidation color development reaction due to peroxidase and does not influence on the color development reaction of hydrogen peroxide due to the leuco dye and peroxidase, i.e., a dye which does not interfere with the maximum absorption wavelength at the time of the leuco dye color development reaction. To be specific, the above-described dyes having the maximum absorption wavelength near 400 to 550 nm may be suitably selected.

As the dye having the maximum absorption wavelength near 400 to 550 nm which can be used in the present invention, food color dyes are, for example, mentioned. Among the food color dyes, usable as synthetic food color dyes are Food Red No. 2 (Amaranth: maximum absorption wavelength of 508 nm), Food Red No. 3 (Erythrosine: maximum absorption wavelength of 526 nm), Food Red No. 40 (Allura Red AC: maximum absorption wavelength of 499 nm), Food Red No. 102 (New Coccine: maximum absorption wavelength of 428 nm), Food Red No. 104 (Phloxine: maximum absorption wavelength of 538 nm), Food Red No. 106 (Acid Red: maximum absorption wavelength of 508 nm), Food Yellow No. 4 (Tartrazine: maximum absorption wavelength of 428 nm), Food Yellow No. 5 (Sunset Yellow FCF: maximum absorption wavelength of 482 nm), etc. Moreover, as dyes other than the food color dyes, Orange G (maximum absorption wavelength of 480 nm), Orange II (maximum absorption wavelength of 480 nm), etc. may also be used. Further, a cochineal dye, an onion dye, a safflower yellow dye, a gardenia red dye, etc., which are known as natural food dyes, can also be used.

A suitable concentration of the dyes having the maximum absorption wavelength near 400 to 550 nm is, for example, in the range of 0.005 to 3 mM and preferably in the range of 0.02 to 1 mM, but is not limited thereto. Moreover, two or more kinds of dyes can be combined for use.

The dyes having the maximum absorption wavelength near 400 to 550 nm may be made to coexist with a leuco dye solution which is stabilized with a reducing agent used for the present invention or may be made to coexist with a peroxidase solution.

The inventors of the present invention conducted extensive research as described above, and, as a result, (1) stabilization of a leuco dye in a liquid state is achieved by causing a reducing agent to coexist and (2) by causing another dye having the maximum absorption wavelength near 400 to 550 nm, at which the absorbance measurement wavelength of the leuco dye is not influenced, to coexist in a solution at the time of a color development reaction, a nonspecific color development of the leuco dye is suppressed. Thus, a reagent composition for quantifying hydrogen peroxide has been accomplished, which contains a leuco dye which has high measurement accuracy, is excellent in practicability, and is stable in a liquid state for a long period of time.

There is no limitation on the application to the analytical reagent composition of the present invention insofar as the application target is a reaction system in which a measurement target can be quantitatively converted to hydrogen peroxide.

Here, as a suitable example, the application of hemoglobin A1c, which is a glycated protein, to an enzymatic measurement method is mentioned. Various enzymatic measurement methods and various measurement enzymes for the hemoglobin A1c have been reported until now as follows.

[Patent Document 4] Japanese Patent Application No. 3034698
[Patent Document 5] WO 2002/06519
[Patent Document 6] WO 2005/56823
[Patent Document 7] Japanese Patent Application Laid-open No. 2001-95598
[Patent Document 8] Japanese Patent Application Laid-open No. 2003-235585
[Patent Document 9] Japanese Patent Application Laid-open No. 2005-110657
[Patent Document 10] WO 2005/49857
[Patent Document 11] WO 2004/104203
[Patent Document 12] WO2006/013921
[Non Patent Document 1] Clinical Chemistry 49 (2): 269-274 (2003)
[Non patent Document 2] Clinical Chemistry and Laboratory Medicine 40 (1): 78-89 (2002)
[Non Patent Document 3] Rinsyokensa 46 (6): 729-734 (2002)

<Glycated hemoglobin>

A glycated hemoglobin refers to as an Amadori compound in which hemoglobin is glycated by the Maillard reaction, and it is said that an α-amino group of valine at an a chain N terminal and a β chain N terminal or an ε-amino group of lysine in a molecule is glycated. A fragment of the glycated hemoglobin refers to a peptide which can be formed by the decomposition of the glycated hemoglobin.

<Hemoglobin A1c>

In the international standard definition, hemoglobin A1c refers to as a hemoglobin in which an α-amino group of valine at a hemoglobin β, chain N terminal is glycated (Clinical Chemistry and Laboratory Medicine 40(1): 78-89 (2002)).

<Ketoamine Oxidase>

Ketoamine oxidase refers to as an enzyme which acts on a compound having a ketoamine structure to generate hydrogen peroxide, and is also referred to as fructosylamine oxidase.

In general, the hemoglobin A1c is quantified using protease and ketoamine oxidase. However, in the international standard definition, since the hemoglobin A1 c is defined as a hemoglobin in which an α-amino group of valine at a hemoglobin β chain N terminal is glycated, the specificity represents an important issue. In a hemoglobin, besides the valine at a β chain N terminal, valine at an α chain N terminal or an ε-amino group of lysine in the molecule is glycated. Therefore, the glycated valine portion only of the hemoglobin β chain N terminal of the hemoglobin A1 c needs to be selectively quantified without measuring the valine at the α chain N terminal or the 1-amino group of lysine in the molecule. As an enzyme for the above-mentioned selective determination, a large number of proteases which cleaves a certain specific product and a large number of ketoamine oxidases which act on a certain specific peptide have been found.

However, even when the protease cleaves a specific product, another peptide or amino acid is usually generated to some extent besides the target product when hemoglobin is used as a substrate. The same applies to the ketoamine oxidase which acts on a certain specific peptide, and there usually exists two or more kinds of substrates on which the ketoamine oxidase acts. More specifically, even when such an enzyme having a high specificity is used, there exist two or more kinds of products which are cleaved from the hemoglobin by the protease. Therefore, it has not yet been reported that only the glycated valine portion of the β chain N terminal of the hemoglobin A1 is measured out based on the independent specificity of the protease alone or the independent specificity of the ketoamine oxidase alone. A method has been reported, which substantially increases the specificity to the glycated valine portion at the hemoglobin β chain N terminal by the combined use of a specific protease and a specific ketoamine oxidase.

For example, Japanese Patent Application Laid-open No. 2001-95598 (Patent Document 7), Japanese Patent Application Laid-open No. 2003-235585 (Patent Document 8), Japanese Patent Application Laid-open No. 2005-110657 (Patent Document 9), WO 2005/49857 (Patent Document 10), WO 2004/104203 (Patent Document 11), and WO 2006/013921 (Patent Document 12), disclose a method of cleaving a glycated valyl histidine by protease from the hemoglobin β chain N terminal, and measuring using ketoamine oxidase which acts on the glycated valyl histidine. Moreover, according to WO 2004/104203 (Patent Document 11), as a method of confirming the substrate specificity of protease, for example, a protease is mentioned, which produces, using a glycated peptide at the α chain N terminal and the β chain N terminal 5 residue of hemoglobin, only a glycated peptide at the β chain N terminal such as glycated valyl histidine, glycated valyl histidyl leucine, and glycated valyl histidyl leucyl threonine, and does not produce glycated valyl leucine derived from the α chain N terminal, glycated valyl leucyl serine, and glycated valyl leucyl seryl proline.

Since the hemoglobin A1 c is measured as a ratio (%) of a glycated substance to a non-glycated substance, not only the measurement of the concentration of the hemoglobin A1c but also the measurement of the total hemoglobin is essential.

The proportion of the hemoglobin A1 c, i.e., hemoglobin A1 c (%), is calculated from the thus-measured ratio of the HbA1c concentration to the total hemoglobin concentration.

The total hemoglobin can be separately measured from the measurement of the hemoglobin-A1c concentration because various measurement methods such as a cyamnethemoglobin method have been reported until now. However, it is desirable that the total hemoglobin and the hemoglobin-A1c concentration can be measured in the same reaction vessel.

For example, WO No. 2006/013921 (Patent Document 12) describes an example of measuring HbA1c in the same reaction vessel in which a protease reaction accelerator which denatures hemoglobin to thereby change the color tone is combined with protease and ketoamine oxidase.

The inventors of the present invention have accomplished an HbA1c measurement reagent excellent in practicability by combining the present invention with the above-described method of measuring a specific hemoglobin A1 c (hereinafter, sometimes referred to as "HbA1c"). More specifically, the inventors of the present invention have accomplished, using, for example, protease and ketoamine oxidase having a high specificity described in WO 2004/104203 (Patent Document 11), an HbA1c determination reagent which is stable in a liquid state and is constituted of two kinds of reagents: one reagent contains a dye which does not react with hydrogen peroxide, peroxidase, and ketoamine oxidase; and another reagent contains a reducing agent, a leuco dye, and protease.

Hereinafter, more suitable examples will be described. The HbA1c determination reagent is constituted of two kinds of liquid reagents, and the following combinations are mentioned.
(Combination 1)
First Reagent:
　Protease reaction accelerator
　Ketoamine oxidase which acts on 1-deoxyfructosyl-L-valyl-L-histidine
　Peroxidase
　Trinder reagent
　Dye which does not react with hydrogen peroxide
Second Reagent:
　Protease which can cleave 1-deoxyfructosyl-L-valyl-L-histidine from a glycated β, chain terminal of HbA1c
　10-(carboxymethylaminocarbonyl)-3,7-bis(dimethylamino)
Phenothiazine Sodium
　Cyclodextrins
　Reducing agent
(Combination 2)
First Reagent:
　Protease reaction accelerator
　Protease which acts on HbA1c to thereby cleave 1-deoxyfructosyl-L-valyl-L-histidine from a glycated β chain terminal of the HbA1c
　10-(carboxymethylaminocarbonyl)-3,7-bis(dimethylamino)
Phenothiazine Sodium
　Catalase
　Cyclodextrins
　Reducing agent
Second Reagent:
　Fructosylamine oxidase
　Peroxidase
　Dye which does not react with hydrogen peroxide The HbA1c determination reagent of the present invention can employ any one of the compositions shown in the above-mentioned combinations. By quantifying the total hemoglobin with the first reagent and quantifying the 1-deoxyfiuctosyl-L-valyl-L-histidine which has been cleaved from the glycated β chain N terminal with the second reagent, a proportion of the hemoglobin A1c to the total hemoglobin amount is calculated. Thus, a measurement reagent which is specific to the HbA1c and is stable in a liquid state has been accomplished.

Here, it should be noted that N,N,N',N',N'',N''-hexa (3-sulfopropyl)-4,4',4''-triaminotriphenylmethane-6 sodium can be also used as a leuco dye in place of 10-(carboxymethylaminocarbonyl)-3,7-bis(dimethylamino) phenothiazine sodium.

Here, the protease reaction accelerator refers to as a compound containing an acetic acid group or its salts, N-acyl taurine or its salts, or polyoxyethylene-alkyl-ether sulfuric acid or its salts, and WO 2006/013921 (Patent Document 12) describes the protease reaction accelerator more specifically. As a suitable example, sodium lauroyl sarcosine (tradename: Sarcosinate LN, product of Nikko chemical Co., Ltd.), sodium myristoyl sarcosine (Sarcosinate MN), sodium lauroyl methylalanine (Alaninate LN-30), etc., can be mentioned.

The trinder reagent in Combination 1 removes peroxide introduced into the first reagent and reduces a reagent blank. For example, usable are N,N-bis (4-sulfobutyl)-3-methylaniline (TODB), N-ethyl-N-(3-sulfopropyl)-3-methoxyaniline (ADPS), N-ethyl-N-(3-sulfopropyl) aniline (ALPS), MAPS, N-ethyl-N-(3-sulfopropyl)-3-methylaniline (TOPS), N-(3-sulfopropyl) aniline (HALPS), N-ethyl-N-(2-hydroxy- 3-sulfopropyl)-3-methoxyaniline (ADOS), ALOS, N-ethyl-N-(2-hydroxy-3-sulfopropyl)-3,5-dimethylaniline (MAOS), N-(3-sulfopropyl)-3,5-dimethoxyaniline (DAPS), HDAPS, N-ethyl-N-(2-hydroxy-3-sulfopropyl)-3,5-dimethoxyaniline (DAOS), etc. The addition concentration thereof is 0.05 to 1 mM. Moreover, in Combination 1, in order to reduce influences of ascorbic acid, ascorbate oxidase can also be added. Further, a surfactant such as bile salt and a salt can also be suitably added.

In addition, in Combination 2, the catalase removes peroxide and reduces a reagent blank, and a readily and commercially available enzyme derived from a bovine liver (Sigma Co., Ltd. and the like) may be used. A suitable concentration thereof is 100 to 2000 u/ml.

In order to measure a ratio of a glycated hemoglobinA1c to a non-glycated hemoglobin using the thus-prepared liquid reagent, blood which has been collected with a blood collecting tube containing an anticoagulant is subjected to centrifugal separation to thereby precipitate a hemocyte portion. The precipitated hemocyte portion is suitably diluted with water using a commercial hemolysis diluter or the like to be hemolyzed. Then, the resultant may be used as a specimen for the measurement.

In addition, especially in the case of Combination 1, when the whole blood is measured, influences of an interfering substance can be avoided. Thus, Combination 1 is desirable. More specifically, as an interfering component which is assumed to be generated from plasma, endogenous glycated peptide is mentioned besides ascorbic acid, bilirubin, and chyle. Therefore, in order to avoid influences of ascorbic acid and the like from a plasma component, ascorbate oxidase and ketoamine oxidase are added to the first reagent to thereby disposing the endogenous glycated peptide and the ascorbic acid, and thus influences of the interfering component to be mixed in a plasma component can be avoided.

Thus, the present invention permits measurement using not only a centrifugally-separated hemocyte but also the whole blood itself, which enables convenient and simple measurement requiring no centrifugation operation.

Hereinafter, Examples of the present invention will be described in detail, but the present invention is not limited to the Examples.

EXAMPLES

Example 1

Effects of Reducing Agents

To a 40 mM Tris-HCl (pH 7.1) solution (hereinafter, sometimes referred to as a "DA-67 solution") containing 0.2 mM DA-67 as a leuco dye solution, each one of N-acetylcysteine, sodium sulfite, sodium disulfite, thioglycerol, sodium thiosulfate, 2-mercaptoethanol, and dithiothreitol was separately added as a reducing agent in such a manner that the concentration of each reducing agent becomes 1 mM and 10 mM (only concentration of dithiothreitol was 1 mM). The resultant solutions were stored without light at 37° C. for 4 days. These solutions were measured for the absorbance of 660 nm immediately after the preparation thereof and 4 days after being stored at 37° C., thereby determining a degree of pigmentation of the leuco dye solution itself before and after the storage.

In addition, a 40 mM Tris-HCl (pH 7.1) solution containing 10 u/ml peroxidase (manufactured by Sigma Co., Ltd.) was separately prepared. To the solution, a 50 μM hydrogen peroxide solution was added and warmed to 37° C. for 5 minutes, and the absorbance of 660 nm of the resultant solution was measured. Then, 0.2 ml of a DA-67 solution, to which the above-mentioned reducing agent had been added, was added. The observation was performed using, as color intensity, a value obtained by subtracting the absorbance from the absorbance measured 5 minutes after the mixing. Here, the absorbance of a solution, to which no hydrogen peroxide was added, was used as a reagent blank. The results are shown in Table 1.

As was clear from Table 1, the initial absorbance of the DA-67 solution alone became 1934 (mAbs) after four days passed in the case where no reducing agent was added. In contrast, the color intensity of systems in which each one of the reducing agents was added was low. It should be noted that a relative % of the color intensity of hydrogen peroxide refers to a relative % at the time when the color intensity on the 0th day of a solution to which no reducing agent was added was defined as 100%.

TABLE 1

| | | Storage days (37° C.) | | | | | | |
|---|---|---|---|---|---|---|---|---|
| | | Degree of pigmentation | | Reagent blank | | Color intensity of hydrogen peroxide | | |
| Reducing agent | mM | 0th day | 4th day | 0th day | 4th day | 0th day | 4th day | Relative (%) |
| No addition | | 28 | 1934 | 35 | 504 | 261 | 228 | 100.0 |
| N-acetylcysteine | 1 | 25 | 1752 | 69 | 431 | 257 | 231 | 98.5 |
| | 10 | 25 | 1996 | 101 | 472 | 243 | 217 | 93.1 |
| Thioglycerol | 1 | 25 | 1318 | 46 | 365 | 260 | 235 | 99.6 |
| | 10 | 24 | 662 | 87 | 181 | 232 | 227 | 88.9 |
| Sodium sulfite | 1 | 25 | 492 | 27 | 114 | 316 | 249 | 121.1 |
| | 10 | 23 | 31 | 25 | 12 | 317 | 179 | 121.5 |
| Sodium disulfite | 1 | 25 | 195 | 26 | 49 | 323 | 244 | 123.8 |
| | 10 | 20 | 21 | 33 | 8 | 305 | 110 | 116.9 |
| Sodium thiosulfate | 1 | 26 | 1974 | 31 | 468 | 266 | 232 | 101.9 |
| | 10 | 28 | 1620 | 37 | 380 | 273 | 236 | 104.6 |
| 2-mercaptoethanol | 1 | 24 | 1624 | 104 | 782 | 251 | 217 | 96.2 |
| | 10 | 26 | 2610 | 162 | 650 | 226 | 205 | 86.6 |
| Dithiothreitol | 1 | 3 | 1385 | 386 | 519 | 255 | 227 | 97.7 | mAbs

Example 2

Effects of Reducing Agents

Each one of various reducing agents was separately added to a 40 mM PIPES buffer solution (pH 7.0) containing 0.1 mM TPM-PS (manufactured by Dojindo Laboratories Co., Ltd.) as a leuco dye solution. The resultants were stored without light at 37° C. for half a year. The absorbance of 600 nm which is near the maximum wavelength of the color development of hydrogen peroxide by TPM-PS was measured, and the results shown in Table 2 were obtained. Among the reducing agents used for the examination, an outstanding effect of inhibiting nonspecific color development was observed in sodium sulfite, sodium disulfite, and sodium thiosulfate.

TABLE 2

|  | 37° C., after half a year | |
| --- | --- | --- |
| Additive | Concentration | Abs (600 nm) |
| Additive free |  | 1.238 |
| HP-β-CD | 2% | 0.135 |
| Sodium sulfite | 5 mM | 0.076 |
| Sodium disulfite | 5 mM | 0.069 |
| Thioglycerol | 5 mM | 1.153 |
| Sodium thiosulfate | 5 mM | 0.154 |
| Cysteamine | 5 mM | 1.53 |
| N-acetylcysteine | 5 mM | 1.46 |

Example 3

Effects of Reducing Agents

To a 40 mMPIPES (pH 6.5) solution containing 0.2 mM DA-67 (hereinafter, sometimes referred to as a "DA-67 solution") and 2% hydroxypropyl-β-cyclodextrin as a leuco dye solution, was separately added, as a reducing agent, each one of N-acetylcysteine, sodium sulfite, sodium disulfite, and thioglycerol in such a manner that the concentration of each reducing agent becomes 1 mM, 2 mM, 5 mM, and 10 mM. The resultant solutions were stored without light at 37° C. for 7 days. These solutions were measured for the absorbance of 660 nm immediately after the preparation thereof and 7 days after being stored at 37° C., thereby determining a degree of pigmentation of the leuco dye solution itself before and after the storage. Next, a reagent blank and color intensity were analyzed using Hitachi 7170 S-type automatic analyzer. More specifically, to 0.18 ml of 40 mM Tris-HCl (pH 7.5) solution containing 10 u/ml peroxidase (Manufactured by Sigma Co., Ltd.) and 5 u/ml ketoamine oxidase (derived from *Curvularia clavata* YH923), was added 0.02 ml of 50 μM glycated valyl histidine (F-VH: PEPTIDE INSTITUTE, INC.). The resultant was warmed to 37° C. for 5 minutes. Then, the absorbance of 660 nm was measured (A1). Next, 0.045 ml each of DA-67 solutions containing any one of the reducing agents each having the above-mentioned concentration was added. Then, observation was performed using, as color intensity, a value obtained by subtracting the absorbance A1 from the absorbance A2 measured 5 minutes after the mixing. Here, the absorbance of a solution to which no F-VH was added was defined as a reagent blank. The results are shown in Table 3.

As was clear from Table 3, the color intensity of DA-67 solutions in the case where F-VH was used as a substrate, the solutions to which each of the reducing agents was added showed a tendency that the color intensity decreased depending on the concentration of the reducing agent. When the concentration of each of the reducing agents, except 10 mM sodium disulfite, reached up to 10 mM, the color intensity of the solution was 80% or higher in the case where the color intensity of the solution to which no reducing agent was added was defined as 100%. In addition, it was revealed that, as compared with the solution to which no reducing agent was added, the reagent blank stored at 37° C. for 4 days decreased depending on the concentration of each of the reducing agents. It should be noted that a relative % of the color intensity of F-VH refers to a relative % at the time when the color intensity on the 0th of a solution to which no reducing agent was added was defined as 100%.

TABLE 3

|  |  | Storage days (37° C.) | | | | | | |
| --- | --- | --- | --- | --- | --- | --- | --- | --- |
|  |  | Degree of pigmentation | | Reagent blank | | F-VH | | |
| Reducing agent | mM | 0th day | 7th day | 0th day | 4th day | 0th day | 4th day | Relative (%) |
| No addition |  | 31 | 844 | 24 | 212 | 251 | 234 | 100.0 |
| N-acetylcysteine | 1 | 28 | 444 | 29 | 114 | 251 | 231 | 100.0 |
|  | 2 | 28 | 475 | 43 | 145 | 248 | 235 | 98.8 |
|  | 5 | 27 | 344 | 49 | 108 | 243 | 232 | 96.8 |
|  | 10 | 27 | 356 | 50 | 92 | 238 | 225 | 94.8 |
| Thioglycerol | 1 | 28 | 455 | 39 | 157 | 245 | 238 | 97.6 |
|  | 2 | 28 | 402 | 48 | 138 | 240 | 236 | 95.6 |
|  | 5 | 27 | 357 | 62 | 110 | 232 | 232 | 92.4 |
|  | 10 | 26 | 225 | 69 | 92 | 223 | 222 | 88.8 |
| Sodium sulfite | 1 | 35 | 197 | 27 | 50 | 271 | 235 | 108.0 |
|  | 2 | 36 | 96 | 32 | 26 | 272 | 224 | 108.4 |
|  | 5 | 34 | 29 | 51 | 11 | 258 | 201 | 102.8 |
|  | 10 | 38 | 12 | 117 | 6 | 219 | 177 | 87.3 |
| Sodium disulfite | 1 | 36 | 82 | 33 | 23 | 271 | 224 | 108.0 |
|  | 2 | 35 | 30 | 45 | 12 | 262 | 212 | 104.4 |
|  | 5 | 28 | 7 | 125 | 5 | 212 | 197 | 84.5 |
|  | 10 | 22 | 2 | 201 | 2 | 107 | 131 | 42.6 |

(mAbs)

Example 4

Effects of Reducing Agents

| (First reagent) | |
|---|---|
| 40 mM | Tris-HCl (pH 7.5) |
| 0.2% | OP-10FF-0 (Nikko Chemicals Co., Ltd.) |
| 0.04 mM | DA-67 |
| 1 mM | Calcium chloride |
| 400 u/ml | Catalase |
| 2% | Hydroxypropyl-β-cyclodextrin |
| | Various reducing agents |

| (Second reagent) | |
|---|---|
| 40 mM | Tris-HCl (pH 7.5) |
| 30 u/ml | FOD (ketoamine oxidase derived from *Neocosmospora vasinfecta* 474) |
| 90 u/ml | Peroxidase |

Measurement was performed using Hitachi 7170 S-type automatic analyzer with the following parameters.

(Measurement of Degree of Pigmentation of DA-67 Solution)

Distilled water was used as a specimen, and the specimen and the first reagent were mixed at a mixing ratio of 2 μl:200 μl. Measurement was performed at one photometry point (point 8). The main wavelength was 660 nm.

(Measurement of Sensitibity (Color Intensity) of Glycated Valyl Histidine (Determination of F-VH))

A specimen, the first reagent, and the second reagent were mixed at a mixing ratio of 20 μl:180 μl:45 μl. Measurement was performed at two photometry points (points 16 and 34). The main wavelength was 660 nm, and the sub wavelength was 800 nm.

(Operation)

Various reducing agents were added to the first reagent containing DA-67. The mixture was put in a brownish-red glass container and stored at 37° C. Each one of thioglycerol (2 mM), N-acetylcysteine (2 mM), and sodium thiosulfate (5 mM) was separately added as a reducing agent to the first reagent. Sampling was performed 3 days after and 7 days after the addition of the reducing agent. Then, a degree of pigmentation, a reagent blank, and sensitivity (color intensity) of glycated valyl histidine (F-VH) were measured.

As shown in Table 4, as compared with a specimen to which no reducing agent was added, the degree of pigmentation of the first reagent decreased in the order of sodium thiosulfate, thioglycerol, and N-acetylcysteine. On the other hand, an addition effect of the reducing agent was observed also with respect to the reagent blank, and the highest addition effect was observed in sodium thiosulfate. The color intensity of the glycated valyl histidine, when the reducing agent was added, was 75 to 89% in the case where the color intensity of a specimen to which no reducing agent was added was defined as 100%.

Example 5

Effects of Combination of Reducing Agents

| (First reagent) | |
|---|---|
| 40 mM | Tris-HCl (pH 7.5) |
| 0.02 mM | DA-67 |
| 1 mM | Calcium chloride |
| 800 u/ml | Catalase |
| 4% | Hydroxypropyl-β-cyclodextrin |
| | Reducing agent |

| (Second reagent) | |
|---|---|
| 40 mM | Tris-HCl (pH 7.5) |
| 30 u/ml | FOD (ketoamine oxidase derived from *Neocosmospora vasinfecta* 474) |
| 90 u/ml | Peroxidase |

The combination effect of N-acetylcysteine which showed a high degree of pigmentation inhibitory effect against the DA-67 containing reagent and sodium thiosulfate showing a high reagent blank inhibitory effect in Example 4 was confirmed. Reducing agents were contained in the first reagent.

Measurement was performed using Hitachi 7170 S-type automatic analyzer with the following parameters.

(Measurement of Degree of Pigmentation of DA-67 Solution)

Distilled water was used as a specimen, and the specimen and the first reagent were mixed at a mixing ratio of 2 μl:200 μl. Measurement was performed at one photometry point (point 8). The main wavelength was 660 nm.

(Determination of Glycated Valyl Histidine)

A specimen, the first reagent, and the second reagent were mixed at a mixing ratio of 20 μl:180 μl:45 μl. Measurement was performed at two photometry points (points 16 and 34). The main wavelength was 660 nm, and the sub-dominant wavelength was 800 nm.

(Operation)

To the first reagent containing DA-67 was added, as a reducing agent, a combination of N-acetylcysteine and sodium thiosulfate so as to have a concentration of 0.5 to 2 mM and 3 to 9 mM, respectively. The resultant was put in a brownish-red glass container and stored at 37° C. Sampling

TABLE 4

| | Storage days (37° C.) | | | | | | | | |
|---|---|---|---|---|---|---|---|---|---|
| | Degree of pigmentation | | | Reagent blank | | | Sensitivity (Glycated VH (20 μM)) | | |
| | First day | 3rd Day | 7th Day | First day | 3rd Day | 7th Day | First day | 3rd Day | 7th Day |
| No addition | 21.6 | 153.1 | 356.0 | 32.8 | 30.6 | 39.1 | 129.0 | 124.6 | 122.3 |
| 2 mM thioglycerol | 2.8 | 24.8 | 43.6 | 18.6 | 18.6 | 35.2 | 97.0 | 94.7 | 103.0 |
| 2 mM N-acetylcysteine | 2.9 | 20.8 | 30.7 | 22.3 | 22.0 | 34.1 | 104.4 | 119.2 | 113.5 |
| 5 mM sodium thiosulfate | 11.9 | 129.8 | 222.3 | 11.7 | 14.9 | 23.1 | 114.4 | 122.0 | 106.5 | mAbs was performed on the first day and the 7th day after the start of the preparation thereof. Then, a degree of pigmentation, a reagent blank, and sensitivity of glycated VH were measured. As shown in Table 5, as compared with a reaction liquid to which no reducing agent was added, the combination of N-acetylcysteine and sodium thiosulfate showed an outstanding effect in any series. The optimal concentration was a combination of N-acetylcysteine having a concentration of 1.5 or 2 mM and sodium thiosulfate having a concentration of 5 mM.

(Measurement of Degree of Pigmentation of DA-67 Solution)

Distilled water was used as a specimen, and the specimen and the first reagent were mixed at a mixing ratio of 2 μl:200 μl. Measurement was performed at one photometry point (point 8). The main wavelength was 660 nm.

(Determination of Glycated Valyl Histidine)

A specimen, the first reagent, and the second reagent were mixed at a mixing ratio of 20 μl:180 μl:45 μl. Measurement was performed at two photometry points (points 16 and 34). The main wavelength was 660 nm, and the sub wavelength was 800 nm.

TABLE 5

| Reducing agent | | Storage days (37° C.) | | | | | |
|---|---|---|---|---|---|---|---|
| | | Degree of pigmentation | | Reagent blank | | Sensitivity (F-VH(20 μM)) | |
| N-acetylcysteine | Sodium thiosulfate | First day | 7th day | First day | 7th day | First day | 7th day | Relative (%) |
| No addition | No addition | 21.2 | 356.0 | 32.8 | 33.1 | 135.9 | 117.5 | 86.5 |
| 0.5 mM | 5 mM | 3.1 | 31.6 | 9.4 | 7.5 | 117.9 | 39.6 | 33.6 |
| 1 | 5 | 2.5 | 18.6 | 9.6 | 7.5 | 108.0 | 62.9 | 58.3 |
| 1.5 | 5 | 2.8 | 12.4 | 8.4 | 7.9 | 102.4 | 78.2 | 76.4 |
| 2 | 5 | 3.1 | 15.0 | 8.5 | 7.9 | 95.5 | 90.7 | 95.0 |
| 2 | 3 | 2.8 | 11.0 | 9.7 | 18.2 | 100.2 | 96.1 | 95.9 |
| 2 | 7 | 2.7 | 15.7 | 7.7 | 8.4 | 91.3 | 124.1 | 135.9 |
| 2 | 9 | 2.8 | 16.7 | 7.0 | 5.0 | 86.0 | 46.9 | 54.6 | mAbs

Example 6

Effects of Reducing Agents in Combination with Another Stabilizing Agent Other than a Reducing Agent (First reagent)

| | |
|---|---|
| 40 mM | Tris-HCl (pH 7.5) |
| 0.02 mM | DA-67 |
| 1 mM | Calcium chloride |
| 1% | MMT (Nikko Chemicals Co., Ltd.) |
| 800 u/ml | Catalase |
| 10% | Ethylene glycol |
| 5k u/ml | Neutral protease (derived from *Bacillus* sp.: Toyobo Co., Ltd.), reducing agent, and hydroxypropyl-β-cyclodextrin |

(Second reagent)

| | |
|---|---|
| 40 mM | Tris-HCl (pH 7.5) |
| 30 u/ml | FOD (ketoamine oxidase derived from *Neocosmospora vasinfecta* 474) |
| 90 u/ml | Peroxidase |

N-acetylcysteine and sodium thiosulfate were used as reducing agents, and hydroxypropyl-β-cyclodextrin was further used in combination. The reducing agents and hydroxypropyl-β-cyclodextrin were contained in the first reagent. Measurement was performed using Hitachi 7170 S-type automatic analyzer with the following parameters.

(Determination of Hemoglobin β Chain N Terminal Glycated Pentapeptide)

With reference to the amino acid sequence of a hemoglobin β chain N terminal, 1-deoxyfructosyl-L-valyl-L-histidyl-L-leucyl-L-threonyl-L-proline (hereinafter, sometimes referred to as "hemoglobin β chain N terminal glycated pentapeptide" (also referred to as "glycated VHLTP")) containing 5 amino acids was synthesized to be used as a substrate.

(Operation)

To the first reagent containing DA-67, N-acetylcysteine and sodium thiosulfate each having a concentration of 2 mM and 5 mM was added hydroxypropyl-β-cyclodextrin so as to have a concentration of 2 to 5%. The mixture was put in a brownish-red glass container and stored at 37° C. Sampling was performed on the first day, the 3rd day, and the 7th day after the start of the preparation thereof. Then, a degree of pigmentation, a reagent blank, and sensitivity of glycated VH and glycated VHLTP were measured. As shown in Table 6, as compared with a reaction liquid to which no reducing agent was added, coloring of a reagent was hardly observed in the sample using N-acetylcysteine and sodium thiosulfate as reducing agents as compared with a control. In addition, when combined with a reducing agent, hydroxypropyl-β-cyclodextrin having a concentration of 2% or higher was sufficient.

TABLE 6

| | | Degree of pigmentation | | | Reagent blank | | | Sensitivity (F-VH) | | | Sensitivity (β-pentapeptide) | | |
|---|---|---|---|---|---|---|---|---|---|---|---|---|---|
| | | Storage days (37° C.) | | | | | | | | | | | |
| Hydroxypropyl-β-cyclodextrin | Reducing agent | First day | 3rd day | 6th day | First day | 3rd day | 6th day | First day | 3rd day | 6th day | First day | 3rd day | 6th day |
| 2% | Absent | 21.2 | 119.8 | 299.3 | 15.5 | 27.6 | 49.5 | 135.8 | 134.2 | 129.5 | 215.0 | 207.0 | 178.0 |
| 2% | Present | 13.6 | 15.8 | 14.8 | 13.5 | 12.9 | 10.6 | 101.6 | 86.9 | 95.4 | 205.4 | 182.4 | 188.5 |
| 4% | Present | 13.2 | 12.9 | 13.3 | 10.9 | 8.9 | 8.1 | 91.3 | 77.6 | 89.3 | 189.2 | 165.4 | 181.7 |
| 5% | Present | 13.3 | 12.6 | 10.9 | 10.3 | 8.0 | 6.9 | 86.8 | 68.8 | 78.7 | 181.4 | 150.4 | 164.7 | mAbs

Example 7

Examination of Sodium Sulfite Amount

| (First reagent) | |
|---|---|
| 40 mM | Tris-HCl (pH 7.5) |
| 500 mM | NaCl |
| 1.0 mM | CaCl$_2$ |
| 0.05% | NaN$_3$ |
| 0.1 mM | ADPS |
| 3.0% | Alaninate LN-30 (Nikko Chemicals Co., Ltd.) |
| 10 u/mL | Peroxidase |
| 15 u/mL | FOD (ketoamine oxidase derived from *Neocosmospora vasinfecta* 474) |

| (Second reagent) | |
|---|---|
| 100 mM | HEPES (8.0) |
| 2.0% | Hydroxypropyl-β-cyclodextrin (HP-β-CD) |
| 0.05% | NaN$_3$ |
| 10 mM | Cholic acid |
| 0 to 3.0 mM | Sodium sulfite |
| 0.10 mM | DA-67 |
| 12 ku/mL | Thermolysin (derived from *Bacillus stearothermophilus*: Daiwa Chemical Co., Ltd.) |

Measurement was performed using Hitachi 7170 S-type automatic analyzer with the following parameters.

As a measurement mode, "two points" were selected, and the concentration of HbA1c or the concentration of glycated VHLTP after the addition of the second reagent was measured. Photometry points were two points (points 16 and 34). The main wavelength was 660 nm, and the sub wavelength was 800 nm.

(Measurement of Degree of Pigmentation of Second Reagent)

Distilled water was used as a specimen, and the specimen and the first reagent were mixed at a mixing ratio of 20 μl:200 μl. Measurement was performed at one photometry point (point 8). The main wavelength was 660 nm. (hemoglobin control determination)

Using a second reagent in which the concentration of sodium sulfite was changed to 3 mM and using hemoglobin control L (4.8%) and hemoglobin control H (10.5%) both of which are commercially available and 50 μM glycated VHLTP as a sample, a degree of pigmentation, a reagent blank, and sensitivity of HbA1c or glycated VHLTP were measured on the first day of the reagent preparation, 10 days after the prepared reagent was cold-stored, and 10 days after the prepared reagent was stored at 37° C. The change amount in the measured absorbance was shown in Table 7. Stabilization of DA-67 was achieved depending on the concentration of sodium sulfite. In contrast, although the sensitivity also decreased depending on the concentration of sodium sulfite, the decrease rate in the sensitivity in the case of 3 mM sulfurous acid was about 25%, which caused no problem in practical use.

TABLE 7

(Table 7-1) Reagent blank and sensitivity of F-VHLTP

| | | Blank | | | | | | F-VHLTP (50-M) | | | | | |
|---|---|---|---|---|---|---|---|---|---|---|---|---|---|
| | | Storage days (cold storage) | | | | Storage days (37° C.) | | Storage days (cold storage) | | | | Storage days (37° C.) | |
| Series | Sodium sulfite (mM) | 0 | 2 | 5 | 10 | 5 | 8 | 0 | 2 | 5 | 10 | 5 | 8 |
| 1 | 0.0 | 37 | 38 | 39 | 42 | 184 | 282 | 346 | 345 | 339 | 348 | 323 | 329 |
| 2 | 0.5 | 20 | 22 | 23 | 25 | 23 | 23 | 323 | 322 | 317 | 322 | 316 | 324 |
| 3 | 1.0 | 16 | 19 | 21 | 21 | 19 | 19 | 302 | 300 | 295 | 301 | 297 | 300 |
| 4 | 1.5 | 14 | 17 | 19 | 20 | 18 | 16 | 285 | 283 | 278 | 283 | 277 | 283 |
| 5 | 2.0 | 12 | 15 | 17 | 18 | 16 | 15 | 272 | 269 | 264 | 269 | 262 | 268 |

TABLE 7-continued

| 6 | 2.5 | 10 | 13 | 15 | 17 | 15 | 14 | 259 | 258 | 252 | 257 | 250 | 255 |
| 7 | 3.0 | 9 | 11 | 14 | 16 | 14 | 13 | 250 | 250 | 241 | 246 | 240 | 244 |
| | | | | | | | | | | | | | (mAbs) |

(Table 7-2) Sensitivities of control VL and control L

| | | VL (Hb: 2 mg/mL) | | | | | L (Hb: 2 mg/mL) | | | | | |
|---|---|---|---|---|---|---|---|---|---|---|---|---|
| | Sodium sulfite | Storage days (cold storage) | | | | Storage days (37° C.) | | Storage days (cold storage) | | | | Storage days 37° C. | |
| Series | (mM) | 0 | 2 | 5 | 10 | 5 | 8 | 0 | 2 | 5 | 10 | 5 | 8 |
| 1 | 0.0 | 2 | 1 | 1 | −1 | −10 | −12 | 27 | 26 | 25 | 25 | 0 | −6 |
| 2 | 0.5 | 3 | 3 | 3 | 2 | 3 | 3 | 29 | 29 | 27 | 27 | 27 | 27 |
| 3 | 1.0 | 4 | 3 | 3 | 3 | 4 | 3 | 29 | 28 | 26 | 26 | 26 | 26 |
| 4 | 1.5 | 4 | 4 | 3 | 3 | 3 | 4 | 28 | 27 | 26 | 24 | 25 | 25 |
| 5 | 2.0 | 5 | 4 | 4 | 3 | 4 | 3 | 28 | 26 | 25 | 24 | 24 | 24 |
| 6 | 2.5 | 5 | 4 | 3 | 3 | 4 | 4 | 27 | 26 | 24 | 23 | 24 | 23 |
| 7 | 3.0 | 5 | 4 | 4 | 3 | 3 | 4 | 26 | 26 | 24 | 23 | 23 | 23 |
| | | | | | | | | | | | | | (mAbs) |

(Table 7-3) Sensitivities of control H and control VH

| | | H (Hb: 4 mg/mL) | | | | | | VH (Hb: 2 mg/mL) | | | | | |
|---|---|---|---|---|---|---|---|---|---|---|---|---|---|
| | Sodium sulfite | Storage days (cold storage) | | | | Storage days (37° C.) | | Storage days (cold storage) | | | | Storage days 37° C. | |
| Series | (mM) | 0 | 2 | 5 | 10 | 5 | 8 | 0 | 2 | 5 | 10 | 5 | 8 |
| 1 | 0.0 | 65 | 64 | 61 | 62 | 32 | 24 | 82 | 79 | 74 | 75 | 52 | 47 |
| 2 | 0.5 | 65 | 63 | 61 | 61 | 59 | 60 | 80 | 76 | 72 | 72 | 71 | 71 |
| 3 | 1.0 | 62 | 60 | 57 | 57 | 56 | 56 | 75 | 71 | 67 | 68 | 67 | 66 |
| 4 | 1.5 | 59 | 57 | 54 | 54 | 53 | 54 | 71 | 67 | 63 | 62 | 62 | 61 |
| 5 | 2.0 | 56 | 54 | 52 | 51 | 50 | 50 | 67 | 64 | 59 | 59 | 59 | 58 |
| 6 | 2.5 | 54 | 53 | 49 | 49 | 48 | 48 | 64 | 61 | 57 | 56 | 56 | 54 |
| 7 | 3.0 | 52 | 51 | 47 | 47 | 46 | 46 | 62 | 58 | 54 | 53 | 53 | 52 |
| | | | | | | | | | | | | | (mAbs) |

(Table 7-4) Degree of Pigmentation: 660 nm

| | Sodium sulfite | Storage days (cold storage) | | Storage days (37° C.) | |
|---|---|---|---|---|---|
| Series | (mM) | 5 | 8 | 5 | 8 |
| 1 | 0.0 | 24 | 38 | 696 | 1164 |
| 2 | 0.5 | 10 | 11 | 12 | 12 |
| 3 | 1.0 | 6 | 6 | 5 | 5 |
| 4 | 1.5 | 4 | 3 | 3 | 3 |
| 5 | 2.0 | 3 | 2 | 3 | 2 |
| 6 | 2.5 | 2 | 2 | 2 | 2 |
| 7 | 3.0 | 2 | 1 | 2 | 2 |
| | | | | | (mAbs) |

Example 8

Effects of Reducing Agents when Stored for a Long Period of Time (First reagent)

Identical to Example 7

(Second reagent)

| 100 mM | HEPES (8.0) |
| 2.0% | Hydroxypropyl-β-cyclodextrin (HP-β-CD) |
| 0.05% | NaN₃ |
| 10 mM | Cholic acid |
| No addition or 2 mM Sodium sulfite | |
| 0.10 mM | DA-67 |
| 12 ku/mL | Thermolysin (derived from *Bacillus stearothermophilus*: Daiwa Chemical Co., Ltd.) |

Measurement was performed using Hitachi 7170 S-type automatic analyzer with the following parameters.

As a measurement mode, "three points" were selected. The total Hb concentration was measured in the first reaction, and the HbA1c concentration was measured in the second reaction. The measurement results were represented by absorbance.

(Measurement of Total Hb Concentration and HbA1 c Concentration)

A commercial hemoglobin control was used as a specimen. The amounts of a specimen, the first reagent, the second reagent were adjusted to 18 μl, 180 μl, and 36 μL, respectively.

The total hemoglobin was measured at photometry point 14, and the HbA1c was measured at photometry points 16 and 34. The main wavelength was 660 nm, and the sub wavelength was 800 nm.

(Measurement of Degree of Pigmentation of Second Reagent)

Measurement of the degree of pigmentation of the second reagent was performed at a main wavelength of 660 nm using distilled water as a specimen. The specimen and the second reagent were mixed at a mixing ratio of 20 μl:200 μl, and measurement was performed at one photometry point (point 8).

A reagent in which 2 mM of sodium sulfite was added to the second reagent containing DA-67 and a reagent in which no sodium sulfite was added to the second reagent containing DA-67 were prepared. The resultants were put in a shielding bottle and cold-stored (5° C.) for six months.

Using hemoglobin control L (4.8%) and hemoglobin control H (10.5%), both of which were commercially available, as samples, a reagent blank and sensitivity were measured based on values measured on the first day of the preparation of the reagent containing 2 mM sodium sulfite as a control. The change amount in the absorbance obtained using a value measured at point 14 corresponding to the Hb concentration and values measured at points 16 and 34 corresponding to the HbA1c concentration is shown in Table 8. The total Hb measurement values did not show the reduction in the sensitivity six months later, irrespective of the existence of sodium sulfite.

In contrast, with respect to the reagent blank, the total hemoglobin and HbA1c, in the case of 2 mM sodium sulfite, hardly changed for six months (the reagent blank in the case of HbA1c was 9.7 mAbs immediately after the preparation thereof and was 8.8 mAbs after six-month cold storage).

In contrast, with respect to the reagent to which no sodium sulfite was added, the absorption of the HbA1c increased to 50.6 mAbs, which was twice or more the value measured at the time of the preparation. Further, in the control measurement results, values from which the reagent blank was subtracted slightly low. This confirmed that the effects of sodium sulfite were notably exhibited also when the DA-67-containing reagent was stored for a long period of time. In the case where sodium sulfite was added, the change in the degree of pigmentation of the reagent itself was not visually observed.

[Reference Example] Determination of the total hemoglobin by protease reaction accelerator described in WO 2006/013921 (Patent Document 12)

| (Reaction solution) | |
|---|---|
| 40 mM | PIPES-NaOH (pH 6.0) |
| 6% | Alaninate LN-30 |
| 4.5 u/ml | Peroxidase |
| 2 mM | Calcium chloride |
| 1 mM | TODB (N,N-bis(4-sulfobutyl)-3-methylaniline (Dojindo Laboratories Co., Ltd.) |

Using a commercial HbA1c control sample and human hemoglobin (manufactured by Sigma Co., Ltd.), a hemoglobin sample was prepared in such a manner that the hemoglobin concentration was in the range of 0 to 60 mg/ml. With a commercial hemoglobin measurement reagent "hemoglobin B-Test Wako" in which a sodium lauryl sulfate method is employed as a principle, hemoglobin was measured to thereby calculate the concentration. Next, 1.8 ml of the reaction liquid was preliminarily warmed at 37° C., and thereafter, 0.2 ml of the same hemoglobin sample was added and mixed. The absorbance at 660 nm 5 minutes later was read. A sample using distilled water in place of a sample was used as a reagent blank, and values obtained by subtracting the reagent blank with respect to the respective samples are shown in Table 9. As is clear from FIG. 1 in which the values are plotted, the difference in the absorbance obtained by using the reaction liquid was in a linear relationship to the hemoglobin concentration until the total hemoglobin reached about 20 mg/ml.

TABLE 9

| Sample No. | Hemoglobin B-test wako Hb (mg/ml) | Determination of the total hemoglobin by protease reaction accelerator mAbs (660 nm) |
|---|---|---|
| 1 | 10.4 | 98.4 |
| 2 | 20.4 | 198.6 |
| 3 | 32.0 | 308.4 |
| 4 | 43.4 | 404.5 |
| 5 | 59.8 | 514.6 |
| 6 | 2.1 | 19.4 |

TABLE 8

| | Sodium sulfite 2 mM | | | | Sodium sulfite none | | | |
|---|---|---|---|---|---|---|---|---|
| | Immediately after preparation | | 6 months later | | Immediately after preparation | | 6 months later | |
| | Hb (ΔmAbs) | HbA1c (ΔmAbs) | Hb (ΔmAbs) | HbA1c (ΔmAbs) | Hb (ΔmAbs) | HbA1c (ΔmAbs) | Hb (ΔmAbs) | HbA1c (ΔmAbs) |
| Reagent blank | 2.1 | 9.7 | 2.2 | 8.8 | 1.8 | 23.0 | 2.3 | 50.6 |
| Control VL | 36.1 | 5.9 | 36.0 | 6.1 | 36.2 | 5.5 | 35.9 | 3.2 |
| Control L | 61.5 | 13.8 | 61.7 | 13.7 | 61.6 | 13.7 | 61.7 | 10.7 |
| Control H | 89.1 | 40.7 | 89.2 | 40.4 | 89.9 | 40.4 | 88.8 | 35.8 |
| Control VH | 68.7 | 54.1 | 68.5 | 53.6 | 68.6 | 52.9 | 68.9 | 48.5 |

TABLE 9-continued

| Sample No. | Hemoglobin B-test wako Hb (mg/ml) | Determination of the total hemoglobin by protease reaction accelerator mAbs (660 nm) |
|---|---|---|
| 7 | 4.3 | 39.7 |
| 8 | 6.7 | 61.2 |
| 9 | 8.9 | 82.4 |
| 10 | 11.3 | 105.0 |
| 11 | 0.5 | 4.5 |
| 12 | 1.0 | 9.4 |
| 13 | 1.6 | 15.3 |
| 14 | 2.1 | 20.0 |
| 15 | 2.7 | 26.0 |
| 16 | 3.5 | 32.9 |
| 17 | 6.7 | 63.9 |
| 18 | 10.5 | 102.3 |
| 19 | 14.4 | 141.9 |
| 20 | 18.6 | 180.8 |

Example 9

Measurement of Total Hemoglobin and Glycated Hemoglobin A1c (Existence or Absence of Reducing Agent)

| (First reagent) | |
|---|---|
| 40 mM | Tris-HCl (pH 7.5) |
| 0.02 mM | DA-67 |
| 2% | HP-β-CD |
| 1% | MMT (Nikko Chemicals Co., Ltd.) |
| 0.5 mM | $CaCl_2$ |
| 10% | Ethylene glycol |
| 5 ku/ml | Neutral proteinase (Toyobo Co., Ltd.) |
| 800 u/ml | Catalase |
| 10 mM | Sodium deoxycholate (Wako Pure Chemical Industries, Ltd.) |
| (Second reagent) | |
| 40 mM | Tris-HCl (pH 7.5) |
| 90 u/ml | Peroxidase |
| 0.05% | $NaN_3$ |
| 31 u/ml | FOD (ketoamine oxidase derived from *Neocosmospora vasinfecta* 474) |

Measurement was performed using Hitachi 7170 S-type automatic analyzer with the following parameters.

As a measurement mode, "three points" were selected, the total Hb concentration was measured in the first reaction, and the HbA1c concentration was measured in the second reaction. The measurement results were represented by absorbance.

(Measurement of Total Hb Concentration and HbA1c Concentration)

The amounts of a specimen, the first reagent, and the second reagent were adjusted to 20 μl, 180 μl, and 45 μl, respectively. The total hemoglobin was measured at photometry point 14, and the HbA1c was measured at photometry points 16 and 34. The main wavelength was 660 nm, and the sub wavelength was 800 nm.

Used as a sample was a solution in which a commercial HbA1c control (a freeze-dried article and a frozen article) was dissolved in such a manner that the hemoglobin concentration became about 0.8 to 5 mg/ml. A sample obtained by adding a reducing agent (1 mM N-acetylcysteine, 5 mM sodium thiosulfate) to the first reagent and a sample to which no reducing agent were measured.

As a measuring mode, "three points" were selected, and then the total Hb concentration was measured in the first reaction, and the HbA1c concentration was measured in the second reaction after the second reagent was added. The amount of each of a specimen, the first reagent, and the second reagent was adjusted to 20 μl, 180 μl, and 45 μl, respectively. The total hemoglobin was measured at photometry point 14, and the HbA1c was measured at photometry points 16 and 34. The total hemoglobin and the HbA1c concentration were subjected to photometry at the main wavelength of 660 nm and at the sub wavelength of 800 nm. The conversion to concentration was performed using glycated β-pentapeptide which was adjusted to a known concentration (manufactured by PEPTIDE INSTITUTE, INC.) in the case of the HbA1c and was performed based on the assigned value of a commercial HbA1c control L (BML) in the case of the total hemoglobin.

Figure 2:
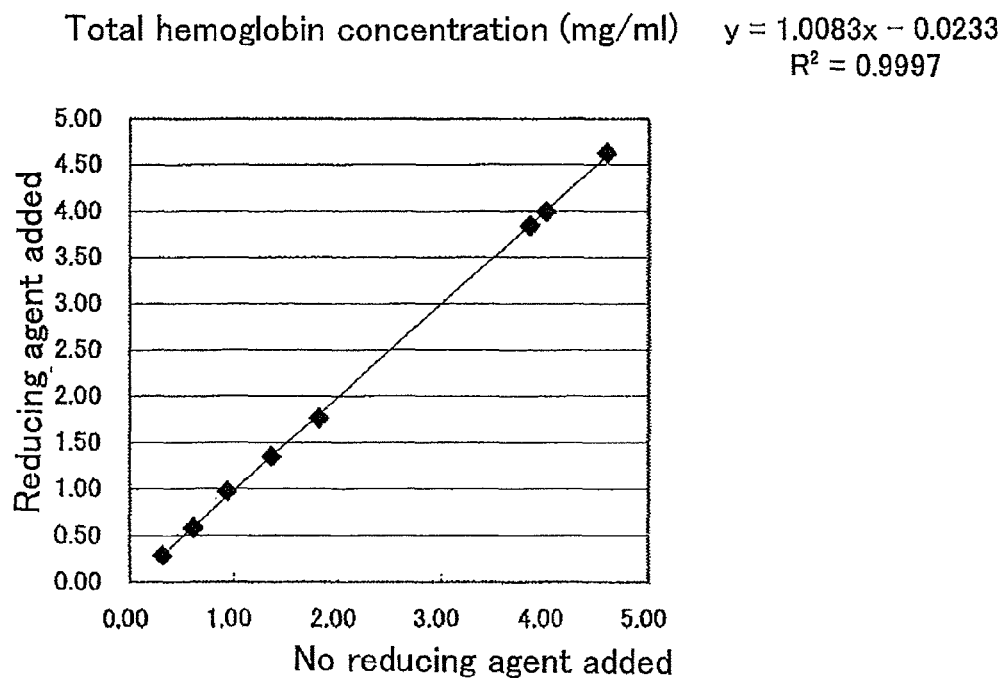
FIG. 2 is a graph illustrating the correlation between a total hemoglobin amount measured by using a reagent containing a reducing agent and a total hemoglobin amount measured by using a reagent not containing a reducing agent.
Figure 3:
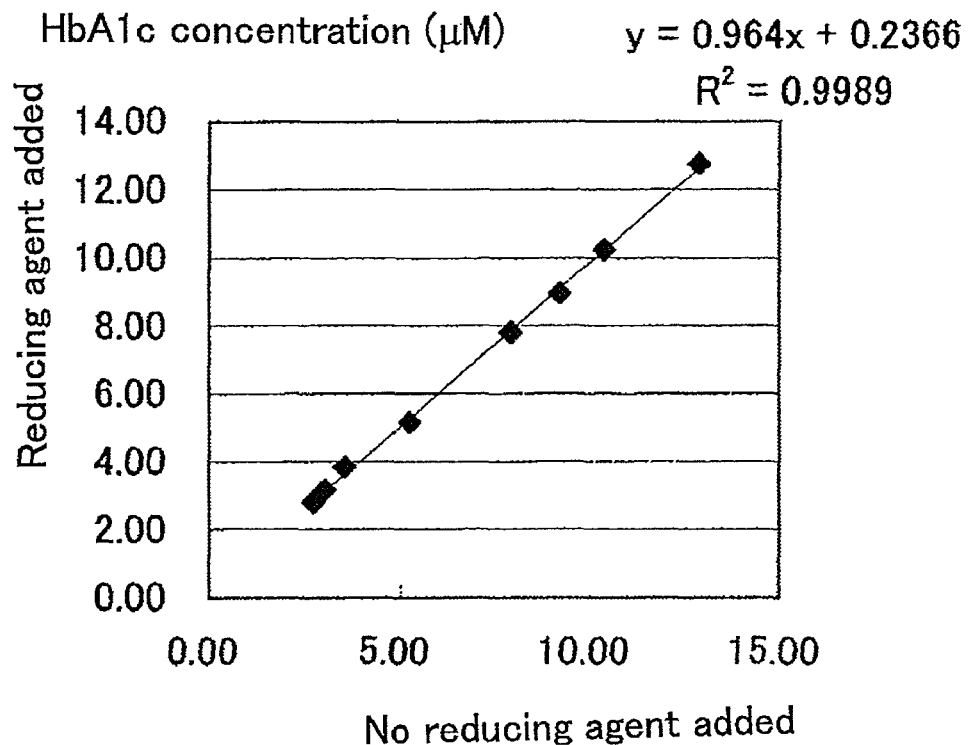
FIG. 3 is a graph illustrating the correlation between a HbA1c amount measured by using a reagent containing a reducing agent and a total hemoglobin amount measured by using a reagent not containing a reducing agent.

As was clear from Table 10, FIG. 2, and FIG. 3, each correlation coefficient of the HbA1c amount and the total hemoglobin amount was excellent (r=0.99 or higher) between when the reducing agent existed and when no reducing agent existed. Thus, influences of the addition of the reducing agent on measurement were not observed.

TABLE 10

| | Reducing agent | | Reducing agent | |
|---|---|---|---|---|
| Sample No. | None Hb (mg/ml) | Added Hb (mg/ml) | None HbA1c (μM) | Added HbA1c (μM) |
| 1 | 4.00 | 4.00 | 3.02 | 3.18 |
| 2 | 3.85 | 3.84 | 9.22 | 8.97 |
| 3 | 4.59 | 4.63 | 3.55 | 3.86 |
| 4 | 0.31 | 0.29 | 2.73 | 2.82 |
| 5 | 0.61 | 0.59 | 5.25 | 5.18 |
| 6 | 0.94 | 0.98 | 7.93 | 7.81 |
| 7 | 1.37 | 1.35 | 10.37 | 10.26 |
| 8 | 1.81 | 1.77 | 12.87 | 12.77 |

Example 10

Measurement of HbA1c (Comparison with Immunoassay Method)

| (First reagent) | |
|---|---|
| 40 mM | Tris-HCl (pH 7.5) |
| 0.02 mM | DA-67 |
| 2% | HP-β-CD |
| 1% | MMT (Nikko Chemicals Co., Ltd.) |
| 0.5 mM | $CaCl_2$ |
| 10% | Ethylene glycol |
| 5 ku/ml | Neutral proteinase (Toyobo Co., Ltd.) |
| 800 u/ml | Catalase |
| 10 mM | Sodium deoxycholate (Wako Pure Chemical Industries, Ltd.) |
| 1 mM | N-acetylcysteine |
| 5 mM | Sodium thiosulfate |
| (Second reagent) | |
| 40 mM | Tris-HCl (pH 7.5) |
| 90 u/ml | Peroxidase |
| 0.05% | $NaN_3$ |
| 31 u/ml | FOD (ketoamine oxidase derived from *Neocosmospora vasinfecta* 474) |

The following measurements were performed using Hitachi 7170 S-type automatic analyzer.

(Immunoassay Method)

Measurement was performed using a "Determiner HbA1c" (product of Kyowa Medex Co., Ltd.) according to the package leaflet. A specimen in which hemocyte was diluted 101 fold with a predetermined specimen diluent for measuring HbA1c was used for measurement.

(The Method of the Present Invention)

Used as the first reagent was a reagent containing DA-67, a reducing agent (N-acetylcysteine and sodium thiosulfate), and protease, and used as the second reagent was a reagent containing ketoamine oxidase and peroxidase.

As a measuring mode, "three points" were selected, and then the total Hb concentration was measured in the first reaction, and the HbA1c concentration was measured in the second reaction after the second reagent was added. The amount of each of a specimen, the first reagent, and the second reagent was adjusted to 20 μL, 180 μl, and 45 μl, respectively. The total hemoglobin was measured at photometry point 14, and the HbA1c was measured at photometry points 16 and 34. The total hemoglobin and the HbA1c concentration were subjected to photometry at the main wavelength of 660 nm and at the sub wavelength of 800 nm. Hemocyte was diluted 71 fold with distilled water to be used as the specimen.

The conversion to concentration was performed based on the assigned value (unit: mg/ml) of a commercial HbA1c control (BML) in the case of the total hemoglobin and was performed based on the absorbance of a glycated valyl histidine (manufactured by PEPTIDE INSTITUTE, INC.) aqueous solution whose concentration was adjusted to a known concentration in the case of the HbA1c concentration. The HbA1c (%) was obtained by dividing the HbA1c concentration by the total hemoglobin concentration. The hemoglobin concentration (M) was calculated by defining the molecular weight of hemoglobin as 64,550.

(Results)

Figure 4:
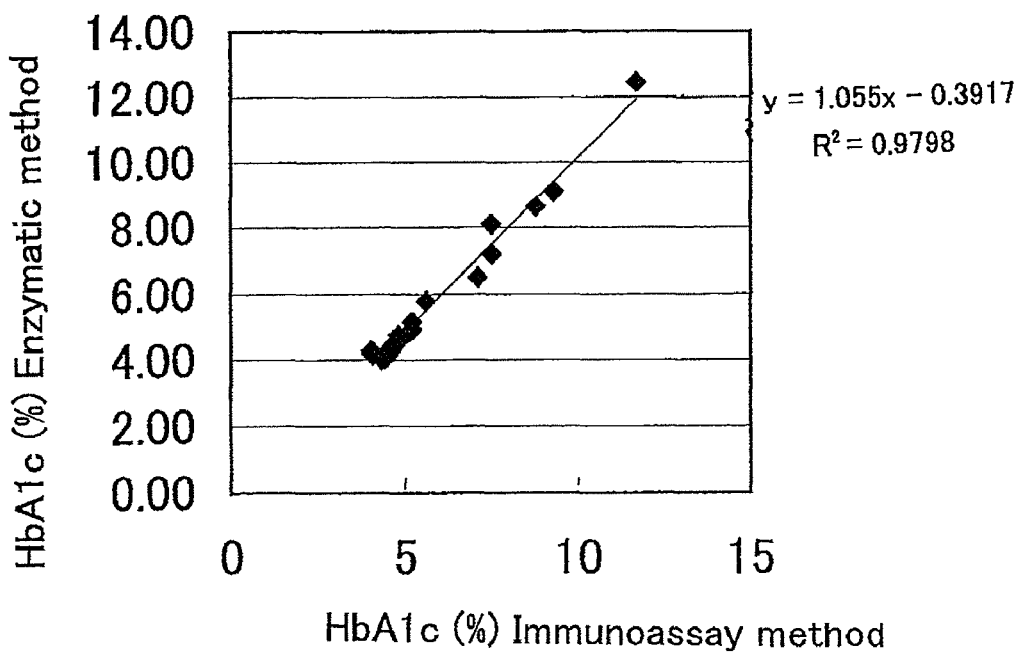
FIG. 4 is an equation graph illustrating the correlation between an immunoassay method and an enzymatic method in which a reagent containing a reducing agent is used.

As shown in FIG. 4, correlation equations when using 22 kinds of specimens were excellent (y=1.055x−0.3917 and R2=0.9798).

Example 11

Dye addition effect when measuring glycated pentapeptide (1-deoxyfructosyl-L-valyl-L-histidyl-L-leucyl-L-threonyl-L-proline) whose sequence is the same as the hemoglobin β chain N terminal sequence)

| (First reagent) | |
|---|---|
| 40 mM | PIPES (pH 7.0) |
| 10 u/ml | POD |
| 0.1 mM | ADOS (Dojindo Laboratories Co., Ltd.) |
| 15 u/ml | FOD (ketoamine oxidase derived from *Neocosmospora vasinfecta* 474) |
| (Second reagent) | |
| 100 mM | Tris-HCl (pH 7.5) |
| 0.12 mM | DA-67 |
| 2 mM | Sodium sulfite |
| 3 ku/ml | Neutral proteinase (Toyobo Co., Ltd.) |

Different two kinds of automatic analyzers manufactured by the following manufacturers were used.

(a) Hitachi automatic analyzer 7170 type

Specimen/First reagent/Second reagent: 20 μl/180 μl/45 μl

Photometry points: two photometry points (points 16 and 34)

Main wavelength: 660 nm

Sub wavelength: 800 nm (b) JEOL BM12 automatic analyzer

Specimen/First reagent/Second reagent: 8 μl/72 μl/18 μl

Photometry points: two-point ends (44 to 47 and 95 to 98)

Main wavelength: 658 nm

Sub wavelength: 805 nm

Using the above-mentioned reagents, the reagent blank was continuously measured 20 times with each automatic analyzer, and the mean absorbance and the standard deviation (SD) were calculated. Next, glycated pentapeptide containing 50 μM hemoglobin β chain N terminal sequence was measured, and then the absorbance from which the reagent blank (mean value of 20 times measurements) was subtracted was calculated. As shown in Table 11, the mean value of 58.8 mAbs of the reagent blank measured by JEOL BM12 was 3 times or more the value of 17.6 mAbs of the reagent blank measured by Hitachi 7170S. In contrast, the absorbance from which the reagent blank of 50 μM glycated pentapeptide was subtracted was almost the same value. The JEOL apparatus showing a high reagent blank value showed a higher standard deviation and inferior measurement accuracy. Then, Yellow No. 4 (product of San-Ei Gen F.F.I., Inc.) of the present invention was added to the first reagent of the reaction liquid in such a manner as to be 0.3 mM, and the same operation was performed. The reagent blank in the case of JEOL BM12 dramatically decreased from 58.8 mAbs to 18.8 mAbs, and the standard deviation also became low. In contrast, the reagent blank in the case of Hitachi 7170 also decreased from 17.6 mAbs to 13.8 mAbs, and the standard deviation also became low. As described above, the difference between the apparatuses observed when Yellow No. 4 was not added was eliminated by adding Yellow No. 4.

TABLE 11

| | | H7170S | | BM12 | |
|---|---|---|---|---|---|
| Yellow No. 4 | | Reagent blank | Glycated pentapeptide | Reagent blank | Glycated pentapeptide |
| None | Absorbance (mAbs) | 17.6 | 274.3 | 58.8 | 276.0 |
| | Standard deviation | 0.286 | | 1.421 | |
| Added | Absorbance (mAbs) | 13.8 | 216.4 | 18.8 | 213.3 |
| | Standard deviation | 0.166 | | 0.217 | |

Example 12

Dye Addition Effects

| (First reagent) | |
|---|---|
| 40 mM | Tris-HCl (pH 7.5) |
| 500 mM | NaCl |
| 0.05% | NaN$_3$ |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |

-continued

| | |
|---|---|
| 10 mM | Cholic acid (Wako Pure Chemical Industries, Ltd.) |
| 15 u/mL | FOD (ketoamine oxidase derived from *Neocosmospora vasinfecta* 474) |

(Second reagent)

| | |
|---|---|
| 100 mM | HEPES (8.0) |
| 2.0% | Hydroxypropyl-β-cyclodextrin (HP-β-CD) |
| 0.05% | NaN$_3$ |
| 10 mM | Cholic acid |
| 2 mM | Sodium sulfite |
| 0.12 mM | DA-67 |
| 12 Ku/mL | Thermolysin (derived from *Bacillus stearothermophilus*: Daiwa Chemical Co., Ltd.) |

JEOL BM1650 automatic analyzer was used.
The parameters were determined as follows.
As an analytical mode, "EPA" was selected. The total Hb concentration was measured in the first reaction after the first reagent had been added, and the HbA1c concentration was measured in the second reaction after the second reagent was added. The amount of each of a specimen, the first reagent, and the second reagent was adjusted to 12 μl, 120μl, and 24 μl, respectively. The total hemoglobin was measured at photometry points 38-41 and the HbA1c was measured at photometry points 44-47 and 95-98. The measurement main wavelength was 658 nm, and the measurement sub wavelength was 805 nm.
ABS was selected as a calculation method, and the calculation results were output as absorbance values.
(Operation)
Reagents were prepared by adding 0.025 mM of Food Red No. 2, 0.15 mM of Food Red No. 102, and 0.25 mM of Food Yellow No. 4 (products of San-Ei Gen F.F.I., Inc.), respectively, to each of the first reagent having the above-mentioned composition. As a control, a reagent containing no dye was prepared. The 4 kinds of first reagents were measured 20 times using distilled water and a commercial HbA1c control (dissolved in such a manner that the HbA1c % became 10%, and the Hb concentration became 2 mg/ml) as a sample, respectively. The absorbance of distilled water was measured to be used as a reagent blank. With respect to the HbA1c control, a subtracted absorbance obtained by subtracting the value of distilled water was output as an absorbance value to each of the total hemoglobin and HbA1c measurement parameters. The maximum absorbance value, the minimum absorbance value, a difference mean value, a standard deviation, and CV % were calculated. The calculation results are shown in Table 12.

As shown in Table 12, there was no influence of the addition of dyes on the measurement values of the total hemoglobin. With respect to the measurement values of the HbA1c, the reagent blank to which no dye was added was 26.4 mAbs. In contrast, the measurement values of the reagents each to which the dye was added were as low as 12 to 15 mAbs, and moreover both the standard deviation and the CV % were lower as compared with those of the reagent to which no dye was added, which showed that the measurement accuracy was improved. With respect to the HbA1c control, the absorbance from which the reagent blank was subtracted decreased to about 70 to 80% of the reagent to which no dye was added. However, both the standard deviation and the CV % were smaller than those of the reagent to which no dye was added.

TABLE 12

| | Non-added | Red No. 2 0.025 mM | Red No. 102 0.15 mM | Yellow No. 4 0.25 mM | Non-added | Red No. 2 0.025 mM | Red No. 102 0.15 mM | Yellow No. 4 0.25 mM |
|---|---|---|---|---|---|---|---|---|
| | Hb measurement: Reagent blank | | | | Hb measurement: Control H | | | |
| Min. | 2.0 | 2.2 | 2.1 | 1.9 | 14.5 | 14.5 | 14.5 | 14.6 |
| Max. | 2.1 | 2.4 | 2.4 | 2.2 | 14.9 | 14.9 | 15.1 | 15.0 |
| Range | 0.2 | 0.2 | 0.3 | 0.3 | 0.4 | 0.4 | 0.5 | 0.5 |
| Mean. | 2.0 | 2.3 | 2.3 | 2.0 | 14.7 | 14.7 | 14.8 | 14.7 |
| S.D. | 0.045 | 0.063 | 0.083 | 0.067 | 0.117 | 0.109 | 0.119 | 0.113 |
| C.V. | 2.20 | 2.73 | 3.66 | 3.29 | 0.80 | 0.74 | 0.80 | 0.76 |
| | HbA1c measurement: Reagent blank | | | | HbA1c measurement: Control H | | | |
| Min. | 25.3 | 12.1 | 14.7 | 12.5 | 25.0 | 17.7 | 21.1 | 20.6 |
| Max. | 27.4 | 12.9 | 15.6 | 13.1 | 26.2 | 18.4 | 21.7 | 21.3 |
| Range | 2.1 | 0.9 | 1.0 | 0.6 | 1.2 | 0.7 | 0.6 | 0.7 |
| Mean. | 26.4 | 12.5 | 15.2 | 12.8 | 25.7 | 18.1 | 21.4 | 20.9 |
| S.D. | 0.768 | 0.229 | 0.287 | 0.200 | 0.355 | 0.195 | 0.183 | 0.196 |
| C.V. | 2.91 | 1.83 | 1.89 | 1.57 | 1.38 | 1.08 | 0.86 | 0.94 |

Example 13

(First reagent)

| | |
|---|---|
| 40 mM | Tris-HCl (pH 7.5) |
| 500 mM | NaCl |
| 0.05% | NaN$_3$ |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |
| 10 mM | Cholic acid (Wako Pure Chemical Industries, Ltd.) |
| 15 u/mL | FOD (ketoamine oxidase derived from *Neocosmospora vasinfecta* 474) |
| | Various dyes |

(Second reagent)

| | |
|---|---|
| 100 mM | HEPES (8.0) |
| 2.0% | Hydroxypropyl-β-cyclodextrin (HP-β-CD) |
| 0.05% | NaN$_3$ |
| 10 mM | Cholic acid |
| 2 mM | Sodium sulfite |
| 0.12 mM | DA-67 |
| 12 ku/mL | Thermolysin (derived from *Bacillus stearothermophilus*: Daiwa Chemical Co., Ltd.) |

Measurement was performed using JEOL BM12 automatic analyzer, and parameters were determined in the same manner as in Example 12.
Reagents were prepared by adding 0.05 mM of Food Red No. 40, 0.4 mM of Food Yellow No. 4, and 1.25 mM of Orange G respectively, to each of the first reagent. As a control, a reagent containing no dye was prepared. The 4 kinds of first reagents were measured 20 times using a commercial low-value HbA1c control (dissolved in such a manner that the HbA1c % became 1.5%, and the Hb concentration became 2 mg/ml) as a specimen. The absorbance of distilled water was measured to be a substitute of a reagent blank. With respect to the HbA1c control, a subtracted absorbance obtained by subtracting the value of distilled water was output as an absorbance value to the HbA1c measurement parameters. The maximum absorbance value, the minimum absorbance value, a difference mean value, a standard deviation, and CV % were calculated. The calculation results are shown in Table 13.

With respect to the measurement values of the HbA1c, the reagent blank (no addition of a dye) was 40.5 mAbs, and in contrast thereto, the measurement values of all of the reagents to which the dye was added were as low as 10 to 13 mAbs. Moreover, both the standard deviation and the CV % were low as compared with the reagent to which no dye was added. Moreover, with respect to a super-low value HbA1c control, the measurement value of the reagent to which no dye was added was smaller (minus value) than the reagent, and the standard deviation was 0.335. In contrast, the absorbance of the reagent to which the dye was added was slightly higher than the reagent blank, and the standard deviation also became low, which showed that the variation in the measurement was improved.

TABLE 13

| | HbA1c measurement: Control VL | | | | |
| --- | --- | --- | --- | --- | --- |
| | Yellow No. 4 0.4 mM | Red No. 40 0.05 mM | Orange G 1.25 mM | No addition | |
| Reagent blank | 10.4 | 11.1 | 12.6 | 40.5 | mAbs |
| Min. | 1.1 | 0.9 | 0.3 | −7.3 | ΔmAbs |
| Max. | 1.7 | 1.2 | 0.7 | −5.9 | ΔmAbs |
| Range | 0.6 | 0.3 | 0.4 | 1.4 | mAbs |
| Mean. | 1.4 | 1.1 | 0.5 | −6.6 | ΔmAbs |
| S.D. | 0.131 | 0.086 | 0.108 | 0.335 | |
| C.V. | 9.05 | 7.94 | 23.36 | −5.09 | |

Example 14

Comparison with Immunoassay Method (Confirmation of Dye Addition Effect)

| (First reagent) | |
| --- | --- |
| 40 mM | BES (pH 7.2) |
| 0.05% | NaN$_3$ |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |
| 10 mM | Cholic acid (Wako Pure Chemical Industries, Ltd.) |
| 15 u/mL | FOD (ketoamine oxidase derived from Neocosmospora vasinfecta 474) |
| | Yellow No. 4 |
| (Second reagent) | |
| 100 mM | HEPES (8.0) |
| 2.0% | Hydroxypropyl-β-cyclodextrin (HP-β-CD) |
| 0.05% | NaN$_3$ |
| 10 mM | Cholic acid |
| 2 mM | Sodium sulfite |

-continued

| | |
| --- | --- |
| 0.12 mM | DA-67 |
| 15 ku/mL | Protease (derived from *Lysobacter enzymogenes* YK-366) |

Using Hitachi 7170 S-type automatic analyzer, a blood specimen collected by a sodium fluoride blood collecting tube was measured as follows.

(Immunoassay Method)

Measurement was performed using a "Determiner HbA1c" (product of Kyowa Medex Co., Ltd.) according to the package leaflet. A specimen in which hemocyte was diluted 101 fold with a predetermined specimen diluent for measuring HbA1c was used for measurement.

(The Method of the Present Invention)

Used as the first reagent was a reagent containing ketoamine oxidase and peroxidase, and used as the second reagent (light-shielding bottle container was used) was a reagent containing DA-67, a reducing agent (sodium sulfite), and protease. As a dye for reducing the reagent blank and maintaining the measurement accuracy, comparison between a reagent in which yellow No. 4 was added to the first reagent and a reagent in which yellow No. 4 was not added to the first reagent was performed.

As a measurement mode, "three points" were selected, the total Hb concentration was measured in the first reaction after the first reagent was added, and the HbA1c concentration was measured in the second reaction after the second reagent was added. The amount of each of a specimen, the first reagent, and the second reagent was adjusted to 20 μl, 180 μl, and 45 μl, respectively. The total hemoglobin was measured at photometry point 14, and the HbA1c was measured at photometry points 16 and 34. Both the total hemoglobin and the HbA1c concentration were measured at a main wavelength of 660 nm and a sub wavelength of 800 nm. Hemocyte after centrifugal separation (1,500G×5 minutes) was diluted 71 fold with distilled water to be used as the specimen.

Calibration was calculated using an HbA1c measurement standard substance JCCLS CRM-004a (HECTEF SRC) by transferring, to a calibrator of our own, the total hemoglobin concentration calculated by a cyanmethemoglobin method and the HbA1c concentration calculated using the HbA1c (%) assigned value of CRM-004a and the hemoglobin concentration.

(Results)

As shown in Table 14, by adding the dye, although a signal of the HbA1c decreased by 20 to 30 percent as compared with a signal of a reagent to which no dye was added, the reagent blank decreased to about the half thereof (11.5 mAbs).

Figure 5:
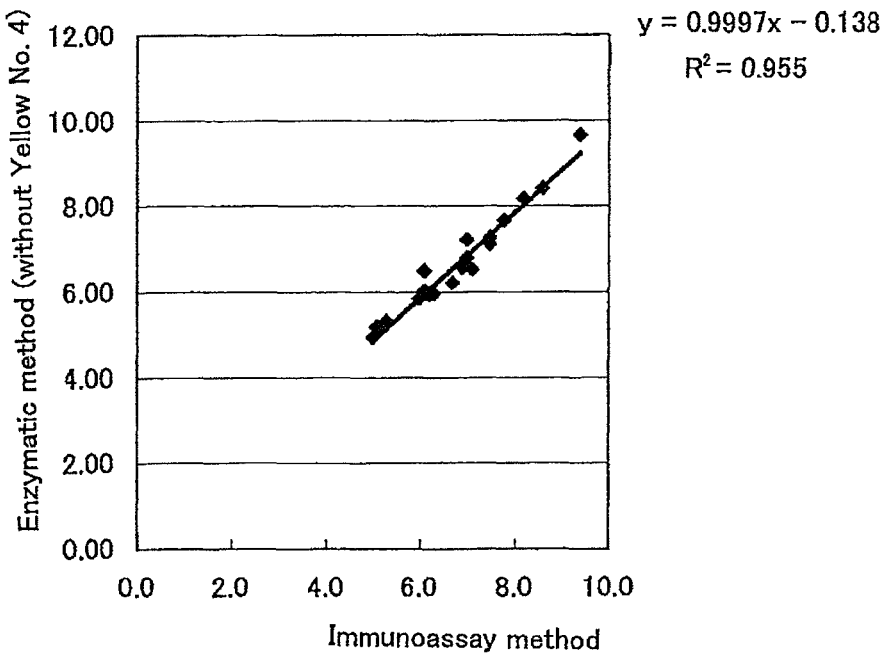
FIG. 5 is an equation graph illustrating the correlation between the immunoassay method and the enzymatic method (with no dye).
Figure 6:
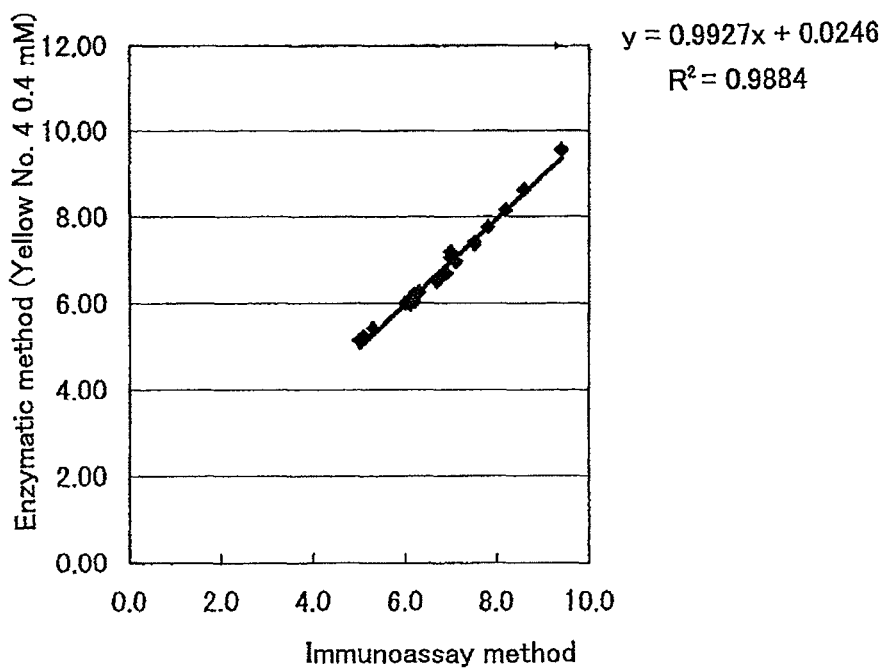
FIG. 6 is an equation graph illustrating the correlation between the immunoassay method and the enzymatic method (with a dye).

With respect to the correlation equation between the immunoassay method (X) and the enzymatic method (Y) when using 20 kinds of specimens, in the case where no Yellow No. 4 was added, y=0.9997x−0.138 and $R^2$=0.955 were indicated, and in the case where Yellow No. 4 was added, y=0.9927x+0.0246 and $R^2$=0.9884 were indicated (FIGS. 5 and 6). It was shown that since the correlation coefficient with the immunoassay method was higher when Yellow No. 4 of the present invention was added, the HbA1c (%) was able to be measured more accurately by the addition of a dye.

TABLE 14

| Specimen No. | Immunoassay method HbA1c % | No Yellow No. 4 added Hb mg/ml | No Yellow No. 4 added HbA1c mg/ml | No Yellow No. 4 added HbA1c % | Yellow No. 4 added Hb mg/ml | Yellow No. 4 added HbA1c mg/ml | Yellow No. 4 added HbA1c % |
|---|---|---|---|---|---|---|---|
| 1 | 5.3 | 4.27 | 0.227 | 5.32 | 4.25 | 0.230 | 5.41 |
| 2 | 7.5 | 4.54 | 0.323 | 7.11 | 4.55 | 0.335 | 7.35 |
| 3 | 6.2 | 4.50 | 0.269 | 5.98 | 4.45 | 0.276 | 6.20 |
| 4 | 7.1 | 5.07 | 0.331 | 6.52 | 5.05 | 0.351 | 6.95 |
| 5 | 8.6 | 4.60 | 0.387 | 8.42 | 4.60 | 0.397 | 8.64 |
| 6 | 7.5 | 4.32 | 0.313 | 7.26 | 4.32 | 0.319 | 7.40 |
| 7 | 6.7 | 4.81 | 0.298 | 6.19 | 4.76 | 0.309 | 6.49 |
| 8 | 8.2 | 4.13 | 0.338 | 8.18 | 4.13 | 0.337 | 8.17 |
| 9 | 7.0 | 4.46 | 0.302 | 6.77 | 4.44 | 0.313 | 7.04 |
| 10 | 5.1 | 4.23 | 0.219 | 5.18 | 4.22 | 0.220 | 5.21 |
| 11 | 6.0 | 4.45 | 0.260 | 5.84 | 4.45 | 0.267 | 6.00 |
| 12 | 6.3 | 4.74 | 0.282 | 5.96 | 4.72 | 0.295 | 6.25 |
| 13 | 6.2 | 4.04 | 0.240 | 5.94 | 4.00 | 0.242 | 6.04 |
| 14 | 9.4 | 3.98 | 0.385 | 9.67 | 4.00 | 0.383 | 9.56 |
| 15 | 7.0 | 4.00 | 0.289 | 7.22 | 4.00 | 0.287 | 7.18 |
| 16 | 6.9 | 4.70 | 0.308 | 6.56 | 4.76 | 0.318 | 6.68 |
| 17 | 5.0 | 4.48 | 0.221 | 4.93 | 4.44 | 0.229 | 5.15 |
| 18 | 6.1 | 3.27 | 0.212 | 6.48 | 3.28 | 0.199 | 6.07 |
| 19 | 6.1 | 3.86 | 0.232 | 6.01 | 3.84 | 0.229 | 5.97 |
| 20 | 7.8 | 4.34 | 0.333 | 7.67 | 4.37 | 0.339 | 7.76 |
| Reagent blank (mAbs) | | 1.40 | 22.00 | | 1.50 | 11.50 | |

Example 15

Accelerated Degradation Test for Stability of Liquid Reagent (First reagent)

| | |
|---|---|
| 30 mM | PIPES-NaOH (pH 7.0) |
| 500 mM | NaCl |
| 0.05% | $NaN_3$ |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |
| 10 mM | Cholic acid (Wako Pure Chemical Industries, Ltd.) |
| 15 u/mL | FOD (ketoamine oxidase derived from *Neocosmospora vasinfecta* 474) |

(Second reagent)

| | |
|---|---|
| 0.6 mM | Yellow No. 4 (San-Ei Gen F.F.I., Inc.) |
| 100 mM | HEPES (8.0) |
| 2.0% | Hydroxypropyl-β-cyclodextrin (HP-β-CD) |
| 0.05% | $NaN_3$ |
| 10 mM | Cholic acid |
| 2 mM | Sodium sulfite |
| 0.12 mM | DA-67 |
| 12 ku/mL | Thermolysin (derived from *Bacillus stearothermophilus*: Daiwa Chemical Co., Ltd.) |

Measurement was performed using Hitachi 7170 S-type automatic analyzer with the following parameters.

As a measuring mode, "three points" were selected, and then the total Hb concentration was measured in the first reaction, and the HbA1c concentration was measured in the second reaction after the second reagent was added. The amount of each of a specimen, the first reagent, and the second reagent was adjusted to 18 μl, 180 μl, and 36 μl, respectively. The total hemoglobin was measured at photometry point 14, and the HbA1c was measured at photometry points 16 and 34. The measurement results were represented by absorbance.

(Variation in Sensitivities of Hemoglobin Control and Pooled Specimen)

Using the above-mentioned reaction liquid (the second reagent was stored in a light-shield bottle container) and using a commercial hemoglobin control (VL (3.5%), L (4.8%), H (10.5%), and VH (16.8%)) and a pooled specimen as a sample, the sensitivity of each of the total hemoglobin and the HbA1c was measured as absorbance. Both the first reagent and the second reagent were cold-stored or stored at 37° C. for 2 weeks. The cold-stored second reagent (in Table 15, R-2 was accelerated degradation) was used for the first reagent stored at 37° C., the cold-stored first reagent (in Table 15, R-1 was accelerated degradation) was used for the second reagent stored at 37° C., and the cold-stored first and second reagents were used for a control (cold storage in Table 15).

As was clear from Table 15, 99% or more of the signal of the total hemoglobin remained, and 94% or more of the signal of the HbA1c remained. In Table 15, figures in brackets refer to the hemoglobin concentration (mg/ml) in the sample. Increase in the reagent blank was not observed even after the second reagent containing the leuco dye DA-67 was treated at 37° C. for two weeks.

TABLE 15

| | | Lapsed days | Reagent blank | VL(2) | L(4) | H(4) | VH(4) | L(3) | H(4.5) | Low POOL | High POOL |
|---|---|---|---|---|---|---|---|---|---|---|---|
| | | | | | | | Hb(mAbs) | | | | |
| mAbs | Control | 0 | 2.3 | 36.7 | 79.6 | 78.6 | 68.0 | 60.1 | 88.4 | 64.8 | 96.9 |
| | Cold storage | 14 | 2.7 | 37.6 | 81.5 | 80.5 | 71.0 | 61.2 | 89.5 | 64.6 | 97.2 |
| | R-1 was accelarated degradation | 14 | 2.7 | 37.8 | 82.0 | 80.4 | 71.2 | 61.8 | 89.9 | 64.9 | 96.9 |
| | R-2 was accelarated degradation | 14 | 2.8 | 37.8 | 81.2 | 80.3 | 71.2 | 61.6 | 89.3 | 64.9 | 96.7 |
| Residual (%) | Control | 0 | | 100.0 | 100.0 | 100.0 | 100.0 | 100.0 | 100.0 | 100.0 | 100.0 |
| | Cold storage | 14 | | 102.5 | 102.4 | 102.4 | 104.4 | 101.8 | 101.2 | 99.7 | 100.3 |
| | R-1 was accelarated degradation | 14 | | 103.0 | 103.0 | 102.3 | 104.7 | 102.8 | 101.7 | 100.2 | 100.0 |
| | R-2 was accelarated degradation | 14 | | 103.0 | 102.0 | 102.2 | 104.7 | 102.5 | 101.0 | 100.2 | 99.8 |
| | | | | | | | HbA1c(mAbs) | | | | |
| mAbs | Control | 0 | 8.7 | 7.2 | 20.5 | 40.5 | 58.6 | 15.5 | 45.0 | 16.6 | 47.2 |
| | Cold storage | 14 | 11.0 | 7.1 | 20.0 | 40.1 | 59.9 | 15.2 | 44.6 | 16.1 | 46.6 |

TABLE 15-continued

|  |  | Lapsed days | Reagent blank | VL(2) | L(4) | H(4) | VH(4) | L(3) | H(4.5) | Low POOL | High POOL |
|---|---|---|---|---|---|---|---|---|---|---|---|
|  | R-1 was accelarated degradation | 14 | 8.0 | 7.9 | 20.6 | 39.2 | 57.5 | 15.7 | 43.1 | 16.5 | 45.1 |
|  | R-2 was accelarated degradation | 14 | 9.1 | 7.2 | 19.7 | 39.3 | 58.9 | 14.9 | 43.4 | 15.6 | 45.2 |
| Residual (%) | Control | 0 |  | 100.0 | 100.0 | 100.0 | 100.0 | 100.0 | 100.0 | 100.0 | 100.0 |
|  | Cold storage | 14 |  | 98.6 | 97.6 | 99.0 | 102.2 | 98.1 | 99.1 | 97.0 | 98.7 |
|  | R-1 was accelarated degradation | 14 |  | 109.7 | 100.5 | 96.8 | 98.1 | 101.3 | 95.8 | 99.4 | 95.6 |
|  | R-2 was accelarated degradation | 14 |  | 100.0 | 96.1 | 97.0 | 100.5 | 96.1 | 96.4 | 94.0 | 95.8 |

Example 16

Stability of Liquid Reagent (First reagent)

| 30 mM | PIPES-NaOH (pH 7.0) |
|---|---|
| 500 mM | NaCl |
| 0.05% | NaN$_3$ |
| 0.5 mM | Calcium chloride |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |
| 10 mM | Cholic acid (Wako Pure Chemical Industries, Ltd.) |
| 15 u/mL | FOD (ketoamine oxidase derived from *Neocosmospora vasinfecta* 474) |
| 0.6 mM | Yellow No. 4 |

(Second reagent)

| 100 mM | HEPES (8.0) |
|---|---|
| 2.0% | Hydroxypropyl-β-cyclodextrin (HP-β-CD) |
| 0.05% | NaN$_3$ |
| 10 mM | Cholic acid |
| 2 mM | Sodium sulfite |
| 0.12 mM | DA-67 |
| 12 Ku/mL | Thermolysin (derived from *Bacillus stearothermophilus*: Daiwa Chemical Co., Ltd.) |

Measurement was performed using Hitachi 7170 S-type automatic analyzer with the following parameters.

As a measuring mode, "three points" were selected, and then the total Hb concentration was measured in the first reaction after the first reagent was added, and the HbA1c concentration was measured in the second reaction after the second reagent was added. The amount of each of a specimen, the first reagent, and the second reagent was adjusted to 18 μl, 180 μl, and 36 μl, respectively. The total hemoglobin was measured at photometry point 14 and the HbA1c was measured at photometry points 16 and 34.

(Variation in Sensitivities of Hemoglobin Control and Pooled Specimen)

Using the above-mentioned reaction liquid (the second reagent was stored in a light-shielding bottle container) and using a commercial hemoglobin control (VL (3.5%), L (4.8%), H (10.5%), and VH (16.8%)) and a pooled specimen as a sample, the sensitivity of each of the total hemoglobin and the HbA1c was measured as absorbance. The first reagent and the second reagent were measured twice: immediately after the preparation thereof; and after cold-stored for 6 months. Calibration was calculated using an HbA1c measurement standard substance JCCLS CRM-004a (HECTEF SRC) by transferring, to a calibrator of our own, the total hemoglobin concentration calculated by a cyanmethemoglobin method and the HbA1c concentration calculated using the HbA1c (%) assigned value of CRM-004a and the hemoglobin concentration.

As was clear from Table 16, the total hemoglobin concentration, the HbA1c concentration, and the HbA1c (%) after stored for six months were equivalent to the values immediately after the preparation thereof. Moreover, the reagent blank did not increase.

TABLE 16

|  | Immediately after preparation | | | 6-month storage | | |
|---|---|---|---|---|---|---|
|  | Hb mg/ml | HbA1c mg/ml | HbA1c % | Hb mg/ml | HbA1c mg/ml | HbA1c % |
| Control VL | 1.93 | 0.075 | 3.89 | 1.93 | 0.080 | 4.14 |
| Control L | 4.20 | 0.203 | 4.83 | 4.19 | 0.207 | 4.94 |
| Control H | 4.12 | 0.404 | 9.82 | 4.12 | 0.407 | 9.89 |
| Control VH | 1.87 | 0.307 | 16.41 | 1.86 | 0.313 | 16.83 |
| Reagent blank (mAbs) | 2.00 | 9.8 |  | 1.70 | 10.7 |  |

Example 17

Measurement Using Whole Blood (First reagent)

| 30 mM | PIPES-NaOH (pH 7.0) |
|---|---|
| 500 mM | NaCl |
| 0.05% | NaN$_3$ |
| 0.5 mM | Calcium chloride |
| 0.1 mM | ALPS (manufactured by Dojindo Laboratories Co., Ltd.) |
| 3.0% | Alaninate LN-30 (Nikko Chemicals Co., Ltd.) |
| 10 u/mL | Peroxidase |
| 10 mM | Cholic acid (Wako Pure Chemical Industries, Ltd.) |
| 15 u/mL | FOD (ketoamine oxidase derived from *Neocosmospora vasinfecta* 474) |
| 0.6 mM | Yellow No. 4 |
| 10 u/mL | Ascorbate oxidase (ASOB: Roche) |

(Second reagent)

| 100 mM | POPSO (8.0) |
|---|---|
| 2.0% | Hydroxypropyl-β-cyclodextrin (HP-β-CD) |
| 0.05% | NaN$_3$ |
| 10 mM | Cholic acid |
| 2 mM | Sodium sulfite |
| 0.12 mM | DA-67 |
| 12 ku/mL | Thermolysin (derived from *Bacillus stearothermophilus*: Daiwa Chemical Co., Ltd.) |

An automatic analyzer BM9020 of JEOL was used.
(Imnunoassay Method)

Measurement was performed using a "Determiner HbA1c" (product of Kyowa Medex Co., Ltd.) according to the package leaflet. A specimen using hemocyte after centrifugal separation was diluted 101 fold with distilled water using a dilution mechanism of BM9020 apparatus, and used for the measurement.

(Method of the Present Invention)

As an analytical mode, "EPA" was selected. The total Hb concentration was measured in the first reaction after the first reagent had been added, and the HbA1c concentration was measured in the second reaction after the second reagent was added. The amount of each of a specimen, the first reagent, and the second reagent was adjusted to 12 µl, 120 µl, and 24 µl, respectively. The total hemoglobin was measured at photometry points 26-28, and the HbA1c was measured at photometry points 29-32 and 62-65. The measurement main wavelength of 596 nm was used for the Hb, and that of 658 nm was used for the HbA1c. The measurement sub wavelength was 805 nm n.

The above-mentioned reaction liquid (the second reagent was stored in a light-shielding bottle container) was used, and a blood specimen collected with a blood collecting tube for blood glucose was used. The specimen was placed in the apparatus after being subjected to end over end agitation before measurement, and diluted 34 fold with distilled water by the dilution mechanism of the apparatus. Calibration was calculated using an HbA1c measurement standard substance JCCLS CRM-004a (HECTEF SRC) by transferring, to a calibrator of our own, the total hemoglobin concentration calculated by a cyanmethemoglobin method and the HbA1c concentration calculated using the HbA1c (%) assigned value of CRM-004a and the hemoglobin concentration.

Figure 7:
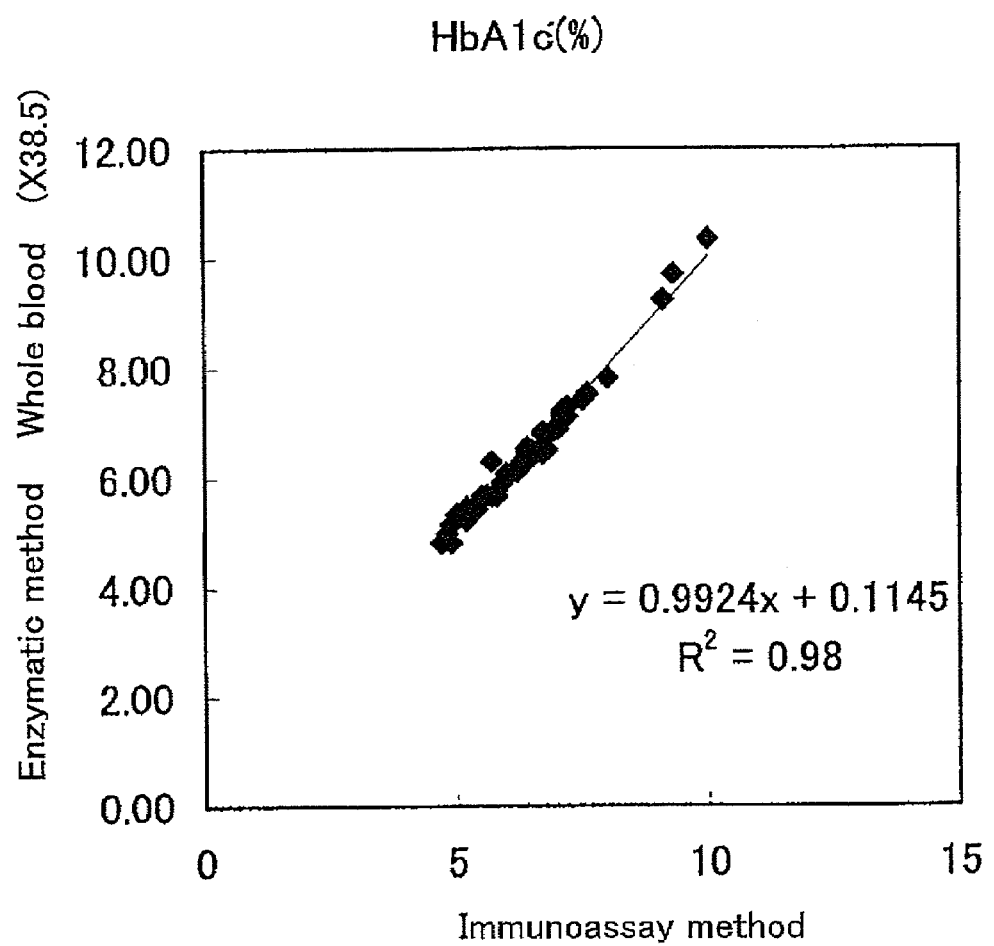
FIG. 7 is an equation graph illustrating the correlation between the immunoassay method (hemocyte) and the enzymatic method (whole blood).

As was clear from Table 17 and FIG. 7, the correlation coefficient between the immunoassay method (using hemocytes) and the enzymatic method (using the whole blood) was excellent (y=0.9924x+0.1145 and $R^2$=0.98). This showed that not only the hemocytes after being subjected to centrifugal separation but also the whole blood before being subjected to centrifugal separation were able to be measured.

TABLE 17

| Specimen No. | Immunoassay method Hemocyte HbA1c % | Method of the present invention Whole blood HbA1c % |
|---|---|---|
| 1 | 5.2 | 5.48 |
| 2 | 6.4 | 6.44 |
| 3 | 7.6 | 7.54 |
| 4 | 6.4 | 6.48 |
| 5 | 6.9 | 6.87 |
| 6 | 5.9 | 5.93 |
| 7 | 6.5 | 6.52 |
| 8 | 6.3 | 6.32 |
| 9 | 7.5 | 7.44 |
| 10 | 7.0 | 6.90 |
| 11 | 5.8 | 5.69 |
| 12 | 6.8 | 6.78 |
| 13 | 6.2 | 6.13 |
| 14 | 5.4 | 5.55 |
| 15 | 5.3 | 5.40 |
| 16 | 5.9 | 5.91 |
| 17 | 6.7 | 6.81 |
| 18 | 7.2 | 7.13 |
| 19 | 6.7 | 6.61 |
| 20 | 4.9 | 4.84 |

TABLE 17-continued

| Specimen No. | Immunoassay method Hemocyte HbA1c % | Method of the present invention Whole blood HbA1c % |
|---|---|---|
| 21 | 5.7 | 5.69 |
| 22 | 8.0 | 7.83 |
| 23 | 4.8 | 4.99 |
| 24 | 7.1 | 7.13 |
| 25 | 6.0 | 6.10 |
| 26 | 5.0 | 5.36 |
| 27 | 7.0 | 6.97 |
| 28 | 7.1 | 7.16 |
| 29 | 6.7 | 6.85 |
| 30 | 5.5 | 5.68 |
| 31 | 5.7 | 6.31 |
| 32 | 7.1 | 7.25 |
| 33 | 6.2 | 6.19 |
| 34 | 4.9 | 5.18 |
| 35 | 5.6 | 5.70 |
| 36 | 6.4 | 6.32 |
| 37 | 5.8 | 5.78 |
| 38 | 6.4 | 6.56 |
| 39 | 5.4 | 5.45 |
| 40 | 7.2 | 7.31 |
| 41 | 7.1 | 7.19 |
| 42 | 6.8 | 6.53 |
| 43 | 5.2 | 5.24 |
| 44 | 9.1 | 9.25 |
| 45 | 9.3 | 9.72 |
| 46 | 6.7 | 6.46 |
| 47 | 5.3 | 5.44 |
| 48 | 5.4 | 5.51 |
| 49 | 10.0 | 10.34 |
| 50 | 6.4 | 6.50 |
| 51 | 4.7 | 4.84 |
| 52 | 7.1 | 7.10 |

The invention can provide a method of stabilizing a leuco dye in a solution, a method of reducing nonspecific color development of the leuco dye at the time of a color development reaction, and an analytical reagent composition for a glycated protein using the methods, and permits accurate measurement of the glycated protein.

What is claimed is:

1. A method of suppressing nonspecific color development in a reaction liquid, the method comprising
combining a dye mixture comprising
a leuco dye and a different dye having an absorption spectrum not influencing a measurement wavelength of the leuco dye and not reacting with hydrogen peroxide,
with hydrogen peroxide and peroxidase, wherein the molar ratio of the different dye to the leuco dye is at least 0.8:1 and no greater than 41.7:1, and wherein the mixture of the different dye with the leuco dye suppresses nonspecific color development in the reaction liquid; wherein the leuco dye comprises 10-(carboxymethylaminocarbonyl)-3,7-bis(dimethylamino)phenothiazine sodium or N,N,N',N',N'',N''-hexa(3-sulfopropyl)-4,4',4''-triaminotriphenylmethane.6 sodium; and
wherein the different dye is selected from the group consisting of Orange G, Food Red No. 2, Food Red No. 40, Food Red No. 102 and Food Yellow No. 4.

2. The method according to claim 1, wherein a maximum absorption wavelength of the different dye is in a range of 400 nm to 550 nm.

3. The method according to claim 1, wherein the reaction liquid comprises a cyclodextrin.

4. The method according to claim 1, wherein the leuco dye is present in a first reagent and the different dye is present in a second reagent, and wherein the first and second reagents are combined to form the dye mixture.

5. The method according to claim 4, wherein the first reagent further comprises a cyclodextrin.

6. The method according to claim 4, wherein the second reagent comprises the peroxidase.

7. The method according to claim 4, wherein the first reagent further comprises a protease.

8. The method according to claim 4, wherein the first reagent further comprises a cyclodextrin and a protease.

9. The method according to claim 4, wherein the second reagent further comprises an oxidase.

10. The method according to claim 1, wherein the molar ratio of the different dye to the leuco dye is at least 1.7:1 and no greater than 41.7:1.

11. The method according to claim 10, wherein the molar ratio of the different dye to the leuco dye is at least 5:1 and no greater than 41.7:1.

12. The method according to claim 1, wherein the molar ratio of the different dye to the leuco dye is at least 0.8:1 and no greater than 25:1.

* * * * *